US007579445B2

(12) United States Patent
Leveugle et al.

(10) Patent No.: US 7,579,445 B2
(45) Date of Patent: Aug. 25, 2009

(54) REAGENTS AND METHODS FOR INDUCING AN IMMUNE RESPONSE TO PROSTATE SPECIFIC ANTIGEN

(75) Inventors: Beatrice Leveugle, Edmonton (CA); Ragupathy Madiyalakan, Edmonton (CA); Antoine A. Noujaim, Edmonton (CA); Birgit C. Schultes, Arlington, MA (US)

(73) Assignee: AltaRex Medical Corp., Edmonton, Alberta (CA)

( * ) Notice: Subject to any disclaimer, the term of this patent is extended or adjusted under 35 U.S.C. 154(b) by 203 days.

(21) Appl. No.: 10/966,789

(22) Filed: Oct. 14, 2004

(65) Prior Publication Data

US 2005/0202018 A1 Sep. 15, 2005

Related U.S. Application Data

(63) Continuation of application No. 09/332,866, filed on Jun. 15, 1999, now Pat. No. 6,881,405.

(60) Provisional application No. 60/089,281, filed on Jun. 15, 1998.

(51) Int. Cl.
*C07K 16/00* (2006.01)
(52) U.S. Cl. ............... 530/387.1; 530/387.7; 530/388.1; 424/130.1; 435/7.1
(58) Field of Classification Search ............... 530/387.1, 530/387.7, 388.1; 424/130.1; 435/7.1
See application file for complete search history.

(56) References Cited

U.S. PATENT DOCUMENTS

| | | | |
|---|---|---|---|
| 3,865,689 A | 2/1975 | Goldenberg | ............... 195/1.7 |
| 4,331,647 A | 5/1982 | Goldenberg | ............... 424/1 |
| 5,053,224 A | 10/1991 | Koprowski et al. | ......... 424/85.8 |
| 5,165,922 A | 11/1992 | Hellstrom et al. | ......... 424/85.8 |

FOREIGN PATENT DOCUMENTS

| | | |
|---|---|---|
| EP | 0 234 122 A2 | 9/1987 |
| EP | 0 308 208 A1 | 3/1989 |
| WO | WO 87/00053 | 1/1987 |
| WO | WO 88/03954 | 6/1988 |
| WO | WO 89/05140 | 6/1989 |
| WO | WO 98/10292 | 3/1998 |

OTHER PUBLICATIONS

Rajakoshi et al, 1997, Prostate Cancer and Prostatic Diseases, 1(1): 16-20.*
Correale et al, Feb. 1997, J Natl Cancer Institute, 89 (4): 293-300.*
Smith, 1994, Clin. Immunol,41: 841-850.*
Boon, 1992 (Adv Can Res, 58:177-210).*
Gura, 1997, (Science, 278:1041-1042).*
Ezzell, 1995 (J. NIH Res, 7:46-49).*
Spitler, 1995 (Cancer Biotherapy, 10:1-3).*
Kirkin et al, 1998, APMIS, 106 : 665-679.*
Sherman et al, 1998, Critical reviews in Immunol, 18 (1-2): 47-54.*
Bowie (Science, 1990, 257 : 1306-1310).*
Roger, I et al, 1988, Bioscience Reports, 8(4): 359-368.*
Mazuwa et al, 1993, Neuroscience Res, 18(1): 27-34.*
Leveugle, B. et al., "PSA-directed immunotherapy of prostate cancer", Proceedings of the American Association for Cancer Research Annual Meeting, vol. 39, Mar. 1988, p. 355 (Abstract).
Correale, P. et al., "In vitro generation of human cytotoxic T lymphocytes specific for peptides derived from prostate-specific antigen", Journal of the National Cancer Institute, vol. 89, No. 4, Feb. 19, 1997, p. 293-300.
Uemura, H. et al., "Generation of anti-idiotype antibodies related to PSA: possible tools for treatment of prostate cancer", Journal of Urology, vol. 153, No. Suppl. 4, 1995, p. 380A (Abstract).
Abbas AK et al., "Antigen presentation by B lymphocytes," *Antigen Presenting Cells: Diversity, Differentiation, and Regulation* 269-279 (1988).
Adams S et al., "Comparison of metabolic and receptor imaging in recurrent medullary thyroid carinoma with histopathological findings," *Eur J Nucl Med*. 25(9):1277-83 (1998).
Alzona M et al., "IL-12 activates IFN-gamma production through the preferential activation of CD30+ T cells," *J Immunol*. 154(1):9-16 (1995).
American Cancer Society, "Cancer Facts and Figures," Atlanta, GA: American Cancer Society (1995).
Andersson K et al., "Modulation of antigen-antibody complexations by immunoglobulins," *Scand J Immunol*. 42(4):407-17 (1995).
Bachmann MF et al., "Regulation of IgG antibody titers by the amount persisting of immune-complexed antigen," *Eur J Immunol*. 24(10):2567-70 (1994).
Barnd DL et al., "Specific, major histocompatibility complex-unrestricted recognition of tumor-associated mucins by human cytotoxic T cells," *Proc Natl Acad Sci U S A*. 86(18):7159-63 (1989).
Bartoloni C et al., "Assay, isolation and characterization of circulating immune complexes from serum of gastrointestinal cancer, stage III and IV melanoma and chronic inflammatory bowel disease patients," *Oncology* 50(1):27-34 (1993).
Bast RC Jr. et al., "A radioimmunoassay using a monoclonal antibody to monitor the course of epithelial ovarian cancer," *New England J. Med*. 309(15):883-7 (1983).
Baum RP et al., "Activating anti-idiotypic human anti-mouse antibodies for immunotherapy of ovarian carinoma," *Cancer* 73(3 Suppl):1121-5 (1994).
Bernard NF et al., "Possible Role for Specific Surface Immunoglobulin In Antigen Presentation," *Antigen Presenting Cells: Diversity, Differentiation, and Regulation* 291-300 (1988).
Boon T et al., "Tumor antigens recognized by T lymphocytes," *Annu Rev Immunol*. 12:337-65 (1994).
Brakenhoff RH et al., "Construction and characterization of the chimeric monoclonal antibody E48 for therapy of head and neck cancer," *Cancer Immunol Immunother*. 40(3):191-200 (1995).

(Continued)

*Primary Examiner*—Larry R. Helms
*Assistant Examiner*—Minh-Tam Davis
(74) *Attorney, Agent, or Firm*—Sheridan Ross P.C.

(57) ABSTRACT

The invention is an apparatus and method for the treatment of prostate cancer, and involves administering an antibody that specifically binds with prostate antigen.

9 Claims, 9 Drawing Sheets

OTHER PUBLICATIONS

Bretscher PA et al., "Establishment of the stable, cell-mediated immunity that makes "susceptible" mice resistant to Leishmania major," *Science* 257(5069):539-42 (1992).

Brockmeyer NH et al., "Immunomodulation of cimetidine in healthy volunteers," *Klin Wochenschr.* 67(1):26-30 (1989).

Bouige P et al., "Immune complexes as immunizing agents to increase the number of monoclonal antibody producing hybrids and to deviate the response to poorly immunogenic epitopes," *Hybridoma* 9(6):519-26 (1990).

Bukowski RM et al., "Phase I trail of continuous infusion interleukin-2 and doxorubicin in patients with refractory malignancies," *J Immunother.* 10(6):432-9 (1991).

Canevari S et al., "Regression of advanced ovarian carinoma by intraperitoneal treatment with autologous T lymphocytes retargeted by a bispecific monoclonal antibody," *J Natl Cancer Inst.* 87(19):1463-9 (1995).

Chang CT et al., "Circular dichroic analysis of protein conformation: inclusion of the beta-turns," *Anal Biochem.* 91(1):13-31 (1978).

Chatterjee MB et al., "Idiotypic antibody immunotherapy of cancer," *Cancer Immunol Immunother.* 38(2):75-82 (1994).

Chester SJ et al., "Improved detection of the early stages of colon cancer by determining both free circulating and immune complex-bound antigens reactive with monoclonal antibody," *Cancer Res.* 54(15):3974-8 (1994).

Cheung NK et al., "Antibody response to murine anti-GD2 monoclonal antibodies: correlation with patient survival," *Cancer Res.* 54(8):2228-33 (1994).

Clarke-Pearson DL et al., "Palliative surgery for epothelial ovarian cancer," In Rub SC, Sutton GP eds. *Ovarian Cancer* New York: McGraw-Hill, Inc. 1993: 351-364.

Crum ED, "Effect of cisplatin upon expression of in vivo immune tumor resistance," *Cancer Immunol Immunother.* 36(1):18-24 (1993).

Defoin A et al.,"A new liquid phase actinometer: Quantum yield and photo-cidnp study of phenylgyoxylic acid in aqueous solution," *J. Photochem.* 33:237-255 (1985).

DiLeo AJ et al., "High resolution removal of virus from protein solutions using a membrane of unique structure," *Biotechnology* 10(2):182-8 (1992).

DiLeo AJ et al., "Size exclusion removal of model mammalian viruses using a unique membrane system, Part II: Module qualification and process simulation," *Biologicals* 21(3):287-96 (1993).

DiLeo AJ et al., "Sixe exclusion removal of model mammalian viruses using a unique membrane system, Part I: Membrane qualification," *Biologicals* 21(3):275-86 (1993).

Dorai, H et al., "Aglycosylated chimeric mouse/human lgG1 antibody retains some effector function," *Hybridoma* 10:211-7 (1991).

Dohlsten M et al., "Monoclonal antibody-superantigen fusion proteins: tumor-specific agents for T-cell-based tumor therapy," *Proc Natl Acad Sci U S A.* 91(19):8945-9 (1994).

Dohlsten M et al., "Antibody-targeted superantigens are potent inducers of tumor-infiltrating T lymphocytes in vivo," *Proc Natl Acad Sci U S A.* 92(21):9791-5 (1995).

Donnerstag B et al., "Immunological profile of patients with ovarian cancer under immunostimulation with murine monoclonal antibodies," *International J. of Oncology* 6:853-858 (1995).

Durrant LG., "Enhanced cell-mediated tumor killing in patients immunized with human monoclonal antiidiotypic antibody 105AD7," *Cancer Res.* 54(18):4837-40 (1994).

Ehrke MJ et al., "Effects of anticancer drugs on the immune system in humans," *Semin Oncol.*16(3):230-5 (1989).

Engvall E and Perlman P, "Enzyme-linked immunosorbent assay (ELISA), Quantitative assay of immunoglobulin G." *Immunochemistry* 8:871 (1971).

Fagerberg J et al., "Induction of an immune network cascade in cancer patients treated with monoclonal antibodies (ab1). I. May induction of ab-1-reactive T cells and anti-anti-idiotypic antibodies (ab3) lead to tumor regression after mAb therapy?," *Cancer Immunol Immunother.* 37(4):264-70 (1993).

Fagerberg J et al., "Induction of an immune network cascade in cancer patients treated with monoclonal antibodies (ab1). ll. Is induction of anti-idiotype reactive T cells (T3) of importance for tumor response to mAb therapy?," *Cancer Immunol Immunother.* 38(3):149-59 (1994).

Fagerberg J et al., "Tumor regression in monoclonal antibody-treated patients correlates with the presence of anti-idiotype-reactive T lymphocytes," *Cancer Res.* 55(9):1824-7 (1995).

Fendrick JL et al., "Characterization of CA 125 synthesized by the human epithelial amnion WISH cell line," *Tumour Biol.* 14(5):310-8 (1993).

Gadducci A et al., "Serum half-life of CA 125 during early chemotherapy as an independent prognostic variable for patients with advanced epithelial ovarian cancer: results of a multicentric Italian study," *Gynecol Oncol.* 58(1):42-7 (1995).

Gallagher G and Al-Azzawi F, "Adoptive immunotherapy of experimental ovarian cancer using activated human monocytes and the human monoclonal antibody, anti-14C1," *Intl J of Oncology* 5:253-258 (1994).

Gallagher G et al., "Multiple epitopes of the human ovarian cancer antigen 14C1 recognised by human lgG antibodies: their potential in immunotherapy," *Br J Cancer* 64(1):35-40 (1991).

Geffner Jr et al., "Activation of human neutrophils and monocytes induced by immune complexes prepared with cationized antibodies or antigens," *Clin Immunol Immunopathol.* 69(1):9-15 (1993).

Goldenberg DM "New developments in monoclonal antibodies for cancer detection and therapy," *CA Cancer J Clin.* 44(1):43-64 (1994).

Goronzy Jet al., "Long-term humoral unresponsiveness in vivo, induced by treatment with monoclonal antibody against L3T4," *J Exp Med.* 164(3):911-25 (1986).

Handgretinger R et al., "A phase I study of human/mouse chimeric antiganglioside GD2 antibody ch14.18 in patients with neuroblastoma," *Eur J Cancer.* 31A(2):261-7 (1995).

Hariharan K eta l., "The induction of cytotoxic T cells and tumor regression by soluble antigen formulation," *Cancer Res.* 55(16):3486-9 (1995).

Harris JE and Braun DP, "Abnormal Immunoregulation and the tumor dormant state in human cancer," In: Stewart THM, Wheelock eds. Cellular immune mechanisms and tumor dormancy, Boca Raton, Florida: CRC Press 261-276 (1992).

Hoskins PJ et al., "Ten-year outcome of patients with advanced epithelial ovarian carcinoma treated with cisplatin-based multimodality therapy," *J Clin Oncol.* 10(10):1561-8 (1992).

Hozumi N and Sandhu JS, "Recombinant antibody technology: its advent and advances," *Cancer Invest.* 11(6):714-23 (1993).

Hayat MA, *Colloidal Gold: Principles, Methods, and Applications* vol. 1, San Diego: Academic Press, Inc. 1989.

Ioannides CG et al., "Cytotoxic T cells from ovarian malignant tumors can recognize polymorphic epithelial mucin core peptides," *J Immunol.* 151(7):3693-703 (1993).

Jacoby RO et al., "Characterization of mouse parvovirus infection by in situ hybridization," *J Virol.* 69(6):3915-9 (1995).

Jensen JL et al., "Possibile utility of serum determinations of CA 125 and CA 27.29 in breast cancer management," *Int. J. Biol. Markers* 6:1 (1991).

Jerne NK, "Towards a network theory of the immune system," *Ann Immunol (Paris)* 125C(1-2:373-89 (1974).

Kehoe S, "Cell-mediated immunity and immunotherapy in ovarian cancer (review)," *Intl J of Oncology* 6:451-458 (1995).

Khazaeli MB et al., "Human immune response to monoclonal antibodies," *J Immunother.* 15(1):42-52 (1994).

Kim HT et al., "Gamma delta T cell recognition of tumor lg peptide," *J Immunol.* 154(4):1614-23 (1995).

Knuth A et al., "T-cell-mediated cytotoxicity against autologous malignant melanoma: analysis with interleukin 2-dependent T-cells cultures," *Proc Natl Acad Sci U S A* 81(11):3511-5 (1984).

Kobayashi H et al., "Characterization of CA 125 antigen identified by monoclonal antibodies that recognize different epitopes," *Clin Biochem.* 26(5):391-7 (1993).

Kosmas C et al., "Activation of cellular immunity after intracavitary monoclonal antibody therapy of ovarian cancer," *Cancer* 73(12):3000-10 (1994).

Kosmas C et al. "Patients receiving murine monoclonal antibody therapy for malignancy develop T cells that proliferate in vitro in response to these antibodies as antigens," *Br J Cancer* 64(3):494-500 (1991).

FT Kreutz and Suresh MR, "Biospecific monoclonal Anti-CA125 X Anti-peroxidase antibodies in the measurement of the ovarian carcinoma antigen," *J of Tumor Marker Oncology* 10(1): 45-53 (1995).

Lamers CH et al., "Inhibition of bispecific monoclonal antibody (bsAb)-targeted cytolysis by human anti-mouse antibodies in ovarian carcinoma patients treated with bsAb-targeted activated T-lymphoctes," *Int J Cancer* 60(4):450-7 (1995).

Lanzavecchia A, "Identifying strategies for immune intervention," *Science* 260(5110):937-44 (1993).

Lanzavecchia A et al., "Antibodies as antigens. The use of mouse monoclonal antibodies to focus human T cells against selected targets," *J Exp Med*. 167(2):345-52 (1988).

Livingston Po et al., "Sympsoium 10: glucosylation defining malignancy. Effect of active immunization with human tumor associated carbohydrate antigens on the immune response and on tumor growth," *Proc. Am. Assoc. Cancer Research* 36:678 (1995).

Loevinger, RL et al., *MIRD Primer for Absorbed Dose Calculations* New York: Society of Nuclear Medicine, 1991.

Lopes LM and Chain BM, "Liposome-mediated delivery stimulates a class I-restricted cytotoxic T cells response to soluble antigen," *Eur J Immunol*. 22(1):287-90 (1992).

Madiyalakan R et al., "Antiidiotype induction therapy: evidence for the induction of immune response through the idiotype network in patients with ovarian cancer after administration of anti-CA125 murine monoclonal antibody B43.13," *Hybridoma* 14(2):199-203 (1995).

Manca F et al., "Effect of antigen/antibody ratio on macrophage uptake, processing, and presentation to T cells of antigen complexed with polyclonal antibodies," *J Exp Med*. 173(1):37-48 (1991).

Maraveyas A and Epenetos AA, "Targeted immunotherpy. An update with special emphasis on ovarian cancer," *Acta Oncol*. 32(7-8):741-6 (1993).

Martin AC et al., "Modeling antibody hypervariable loops: a combined algorithm," *Proc Natl Acad Sci U S A* 86:9268-72 (1986).

Marusic-Galesic S et al., "Cellular immune response to the antigen administered as an immune complex," *Immunology*. 72(4);526-31 (1991).

Meier W, "CA 125 based diagnosis and therapy in recurrent ovarian cancer," Abstract. *Abstarcts of the Eighth International Hamburg Symposium on Tumor Markers Hamburg*, Germany 2443 (1995).

Mitchell MS, *Biological Approaches to Cancer Treatment: Biomodulation* New York: McGrawHill, Inc., 1993.

Mitchell MS et al., "Biomodulates in cancer treatment," *J Clin Pharmacol*.32(1):2-9 (1992).

Mosmann TR and RL Coffman, Two types of mouse helper t-cell clone, Review. *Immunology Today* 8(7 and 8):223-227 (1987).

Muddukrisha SN et al., "Indirect iodometric procedure for quantation of Sn(II) in radiopharmaceutical kits," *Appl. Radial. Isot.* 45(3):293-299 (1994).

Munn DH and Cheung NK "Interleukin-2 enhancement of monoclonal antibody-mediated cellular cytotoxicity against human melanoma," *Cancer Res*. 47(24 Pt 1):6600-5 (1987).

Naramura M et al., "Therapeutic potential of chimeric and murine anti-(epidermal growth factor receptor) antibodies in a metastasis model for human melanoma," *Cancer Immunol Immunother*. 37(5):343-9 (1993).

National Cancer Institute of Canada, "Canadian Cancer Statistics" Toronto: National Cancer Institute of Canada (1998).

Nemazee DA and Sato VL, "Enhancing antibody: a novel component of the immune response," *Proc Natl Acad Sci U S A*. 79(12):3828-32 (1982).

Ohta S et al., "Tumor-associated glycoantigen, sialyl Lewis$^a$ as a target for bispecific antibody-directed adoptive tumor immunotherapy," *Immunol Lett*. 44(1):35-40 (1995).

Ovarian Cancer: Screening, Treatment, and Followup. NIH Consens Statement 12(3):1-30 (1994).

Ozols, MD, PhD, RF "Biologic Treatment of Human Cancer," *Current Problems in Cancer* 19(4):186-261 (1995).

Pederson J et al., "Antibody Modeling: Beyond Homology," *Immunomethods* 1:126-136 (1992).

Perala-Heape M et al., "Effects of tumour mass and circulating antigen on the biodistribution of 111In-labelled F(ab')2 fragments of human prostatic acid phosphatase monoclonal antibody in nude mice bearing PC-82 human prostatic tumour xenografts," *Eur J Nucl Med*. 18(5):339-45 (1991).

Pierce SK and LA Casten, "Soluble globular protein antigens covalently coupled to antibodies specific for b cell surface structures are effective antigens both in vitro and in vivo," *Antigen presenting cell: diversity, differentiation, and regulation* 259-268 (1988).

Pimm MV, "Circulating antigen: bad or good for immunoscintigraphy?" *Nucl Med Biol*. 22(2):137-45. Review. (1995).

Pimm MV et al., "Influence of syngeneic monoclonal anti-idiotypic antibodies to murine monoclonal antibodies against tumour-associated antigens on the biodistribution of their target antibodies and their fragments," *J Cancer Res Clin Oncol*. 119(7):408-14 (1993).

Pimm MV and Gribben SJ, "Toxicity associated with the formation and clearance of immune complexes between antitumour monoclonal antibodies and syngeneic anti-idiotypic antibodies in mice," *J Cancer Res Clin Oncol*. 119(1):41-5 (1992).

Provencher SW and Glockner J, "Estimation of globular protein secondary structure from circular dichroism," *Biochemistry* 20(1):33-7 (1981).

Randall RE et al., "Purification of antibody-antigen complexes containing recombinant SIV proteins: comparison of antigen and antibody-antigen complexes for immune priming," *Vaccine* 12(4):351-8 (1994).

Riethmuller G et al., "Monoclonal antibodies in cancer therapy," *Curr Opin Immunol*. 5(5):732-9 ( 1993).

Riethmuller G et al., "Randomised trial of monoclonal antibody for adjuvant therapy of resected Dukes' C colorectal carcinoma," *Lancet* 343(8907):1177-83 (1994).

Ron IG et al., "Use of CA-125 response to predict survival parameters of patents with advanced ovarian carcinoma," *Acta Obstet Gynecol Scand*. 73(8):658-62 (1994).

Roosnek E and A Lanzavecchia, "Efficient and selective presentation of antigen-antibody complexes by rheumatoid factor B cells," *J Exp Med*. 173(2):487-9 (1991).

Schlebusch H et al., "A monoclonal antiidiotypic antibody ACA 125 mimicking the tumor-associated antigen CA 125 for immunotherapy of ovarian cancer," *Hybridoma* 14(2):167-7 (1995).

Schmolling J et al., "Antiidiotypic antibodies in ovarian cancer patients treated with the monoclonal antibody B72.3," *Hybridoma* 14(2):183-6 (1995).

Schultes BC et al., "Idiotypic cascades after injection of the monoclonal antibody OC125: a study in a mouse model. Induction of antibodies against OC125 and CA 125 after immunization with an anti-CA 125 (MAb OC125) monoclonal antibody by activation of the idiotypic network," *Eur J Clin Chem Clin Biochem*. 31(7):427-32 (1993).

Sciammas R et al., "TCR gamma delta cells: mysterious cells of the immune system," *Immunol Res*. 13(40:268-79 (1994).

Shitara K et al., "A mouse/human chimeric anti-(glanglioside GD3) antibody with enhanced antitumor activities," *Cancer Immunol Immunother*. 36(6):373-80 (1993).

Snyder et al., *A Tabulation of Dose Equivalent per Microurie-Day for Source and Target Organs of an Adult for Various Radionuclides* Oak Ridge National Laboratory, Oak Ridge T- (1975).

Spalding BJ, "Few firms pursue anti-ids," *Bio/Technology* 10:950 (1992).

Squire CM et al., "Antigen presentation is enhanced by targeting antigen to the Fc epsilon Fll by antigen-anti-Fc epsilon Rll conjugates," *J Immunol*. 152(9):4388-96 (1994).

Stevenson FK and RE Hawkins, "Molecular Vaccines Against Cancer," *Immunologist* 2(1):15-19 (1994).

Strieter RM et al., "Cellular and molecular regulation of tumor necrosis factor-alpha production by pentoxifylline," *Biochem Biophys Res Commun*. 155(3):1230-6 (1988).

Sulica A et al., "Regulation of human natural cytotoxicity by IgG. IV. Association between binding of monomeric IgG to the Fc receptors on large granular lymphocytes and inhibition of natural killer (NK) cell activity," *Cell Immunol.* 147(2):397-410 (1993).

Taggart, RT, Samloff IM., "Stable antibody-producing murine hybridomas," *Science* 219:1228-1230 (1983).

Tew JG et al., "Induction of the secondary antibody response: immune complex formation, iccosome release by follicular dendritic cells, processing and presentation of antigen by genminal center b cells and tingible body macrophages," *Progress in Leukocyte Biology* 7:1-10 Alan R Liss, Inc., New York (1988).

Thomson AW and JV Forrester, "Therapeutic advances in immunosuppression," *Clin Exp Immunol.* 98(3):351-7 (1994).

Torbett BE et al., "hu-PBL-SCID mice: a model for human immune function, AIDS, and lymphomagenesis," *Immunol Rev.* 124:139-64 (1991).

Trauth BC et al., "Monoclonal antibody-mediated tumor regression by induction of apoptosis." *Science* 245(4915):301-5 (1989).

Ullman EF et al., "Anti-immune complex antibodies enhance affinity and specificity of primary antibodies," *Proc Natl Acad Sci U S A.* 90(4):1184-9 (1993).

United Nations, Demographic Yearbook, 1992 Forty-fourth issue, New York (1994).

United Nations Population Fund, The State of World Population, 1991.

van der Bruggen p, "The long-standing quest for tumor rejection antigens," *Clin Immunol Immunopathol* 71(3):248-52 (1994).

Vitetta ES and JW Uhr, "Monoclonal antibodies as agonists: an expected role for their use in cancer therapy," *Cancer Res.* 54(20):5301-9 (1994).

Vose BM and Bonnard GD, "Specific cytotoxicity aganist autologous tumour and proliferative responses of human lymphocytes grown in interleukins 2," *Int J Cancer* 29(1):33-9 (1982).

Wagner U, "Antitumor antibodies for immunotherpy of ovarian carcinomas," *Hybridoma* 12(5):521-8 (1993).

Wagner U et al., "Clinical courses of patients with ovarian carcinomas after induction of anti-idiotypic antibodies against a tumor-associated antigens," *Tumor Diagnostic & Therapic* 11:1-4 (1990).

Wagner UA et al., "Immunotherapy of advanced ovarian carcinomas by activation of the idiotypic network," *Biotechnol Ther.* 3(1-2):81-9 (1992).

Walker AM et al., "Prolactin-immunoglobulin G complexes from human serum act as costimulatory ligands causing proliferation of malignant B lymphocytes," *Pro Natl Acad Sci U S A.* 92(8):3278-82 (1995).

Wawrzynczak EJ et al., "Blood clearance in the rat of a recombinant mouse monoclonal antibody lacking the N-linked oligosaccharide side chains of the CH2 domains," *Mol Immunol.* 29:213-20 (1992).

Wiersma EJ et al., "Enhancement of the antibody response to protein antigens by specific lgG under different experimental conditons," *Scand J Immunol.* 36(2):193-200 (1992).

Wolff EA et al., "Monoclonal antibody homodimers: enhanced anti-tumor activity in nude mice," *Cancer Res.* 53(11):2560-5 (1993).

Wyatt, PJ "Light scattering and the absolute characterization of macromolecules" Review. *Analytica Chimica Acta* 272:1-40 (1993).

Xu ZY et al., "Overcoming suppression of antitumor immune reactivity in tumor-bearing rats by treatment with bleomycin," *Cancer Res.* 48(23):6658-63 (1988).

Yano S et al., "Natural antibody against the immunoglobulin F(ad')2 fragment cause elimination of antigens recognized by the F(ab')2 from the circulation," *Eur J Immunol.* 25(11):3128-33 (1995).

Zhang S et al., "Increased tumor cell reactivity and complement-dependent cytotoxicity with mixtures of monoclonal antibodies against different gangliosides," *Cancer Immunol Immunother.* 40(2):88-94 (1995).

\* cited by examiner

| E | E | | | | | | | | |
|---|---|---|---|---|---|---|---|---|---|
| 139 | 140 | | | | | | | | |
| F | L | T | P | K | K | L | Q | C | V |
| 141 | 142 | 143 | 144 | 145 | 146 | 147 | 148 | 149 | 150 |
| D | L | H | V | I | S | N | D | V | C |
| 151 | 152 | 153 | 154 | 155 | 156 | 157 | 158 | 159 | 160 |
| A | Q | V | | | | | | | |
| 161 | 162 | 163 | | | | | | | |

(Seq ID No.: 1)

SEQUENCE LISTING

```
<160> NUMBER OF SEQ ID NOS: 4

<210> SEQ ID NO 1
<211> LENGTH: 25
<212> TYPE: PRT
<213> ORGANISM: Homo sapiens

<400> SEQUENCE: 1

Glu Glu Phe Leu Thr Pro Lys Lys Leu Gln Cys Val Asp Leu His Val
 1               5                  10                  15

Ile Ser Asn Asp Val Cys Ala Gln Val
                20                  25

<210> SEQ ID NO 2
<211> LENGTH: 10
<212> TYPE: PRT
<213> ORGANISM: Homo sapiens

<400> SEQUENCE: 2

Phe Leu Thr Pro Lys Lys Leu Gln Cys Val
 1               5                  10

<210> SEQ ID NO 3
<211> LENGTH: 9
<212> TYPE: PRT
<213> ORGANISM: Homo sapiens

<400> SEQUENCE: 3

Lys Leu Gln Cys Val Asp Leu His Val
 1               5

<210> SEQ ID NO 4
<211> LENGTH: 10
<212> TYPE: PRT
```

```
<213> ORGANISM: Homo sapiens

<400> SEQUENCE: 4

Val Ile Ser Asn Asp Val Cys Ala Gln Val
 1               5                   10
```

REAGENTS AND METHODS FOR INDUCING AN IMMUNE RESPONSE TO PROSTATE SPECIFIC ANTIGEN

RELATED APPLICATION

This application is a continuation of U.S. application Ser. No. 09/332,866 filed on Jun. 15, 1999, now, U.S. Pat. No. 6,881,405, which claims the benefit of U.S. Provisional Application No. 60/089,281 filed on Jun. 15, 1998. The entire teachings of U.S. application Ser. No. 09/332,866 are incorporated herein by reference.

TECHNICAL FIELD OF THE INVENTION

The present invention relates generally to the generation of cellular and humoral immune responses to prostate-specific antigen (PSA). The present invention also relates to a therapeutic composition that contains a monoclonal antibody that is useful in generating cellular and humoral immune responses to PSA.

BACKGROUND OF THE INVENTION

Prostate cancer is one of the most common cancers in men and is one of the most common causes of cancer death, although, if diagnosed early, is potentially curable through surgical intervention, radiation therapy, or hormonal therapy. Since differential diagnosis is difficult at best, however, most prostate cancer is not diagnosed until later stages, typically after metastasis of the primary tumor. The primary therapy for metastatic prostate cancer is either androgen-antagonistic agents or castration, but most relapse patients show prostate tumor cells that are androgen-independent. Currently, there are no effective chemotherapeutic agents that can control the growth of androgen-independent prostate tumor cells.

PSA is a 240 amino acid member of the glandular kallikrein gene family. This 33 kDa single chain glycoprotein is a serine protease secreted by both normal and transformed epithelial cells of the prostate gland. PSA can be detected at low level in the sera of healthy males without evidence of prostate cancer. However, during neoplastic states, circulating levels of this antigen increase markedly, correlating with the clinical stage of the disease. PSA expression is almost exclusively restricted to the prostate cells, and is the most widely used marker for the diagnosis and monitoring of prostate cancer patients.

The tissue specificity of PSA makes it a particularly attractive target antigen for the development of immunotherapies against prostate cancer. PSA is detected in nearly all adenocarcinomas of the prostate and the expression of PSA was also demonstrated at distant metastatic sites. Several studies point out that PSA is a potential target for the induction of T-cell directed immunity against prostate cancer. Indeed, several PSA peptides capable of binding to MHC-class I molecules have been identified and it is now well established that a PSA specific T-cell repertoire exists in humans. Studies using in vitro immunization have shown the generation of CD4 and CD8 cells specific for PSA and T-cell lines with specific recognition of PSA peptides were generated from both healthy volunteer and prostate cancer patients. Of particular importance is the generation in vitro of cytotoxic T-lymphocytes specific for PSA and capable of lysing human prostate tumor cells [Xue et al., *Prostate* 30(2):73-8, (1997); Correale et al., *Journal of the National Cancer Institute* 89(4):293-300 (1997); Correale et al., *Journal of Immunology* 161 (6):3186-94 (1998); Alexander et al., *Urology* 51(1):150-7 (1998)].

Based on these promising data, numbers of PSA-targeted immunotherapeutic approaches are currently being investigated in preclinical setting. Clinical trials employing a recombinant vaccinia virus engineered to express PSA, recombinant PSA encapsulated into liposomes, or autologous dendritic cells loaded with peptide sequences of PSA have already started [See *Future Oncology* Vol 4, No. 3/4 (1998)].

The present invention describes a new immunotherapeutic product for prostate cancer that employs as a therapeutic agent a binding agent such as a monoclonal antibody directed against PSA. It is believed that the therapeutic efficacy of the injected anti-PSA antibody is based on multiple mechanisms of actions acting in synergy. Tumor cell killing through an ADCC or CDC mechanism is not expected for these binding agents since PSA is not expressed at the cell surface. The therapeutic efficacy of these binding agents relies on the induction of a specific PSA cellular immune response and in the non-specific stimulation of the host immune system resulting in the induction of an immune response against various tumor antigens.

The induction of a specific cellular immune response upon immunization of the host with either Ab1 or Ab2 has been demonstrated in a number of studies. Of particular importance is the generation through this mechanism of specific CTLs responses in ovarian cancer patients, melanoma patients, myeloma patients, and non-Hodgkin's lymphoma patients [Nelson et al., *Blood* 88(2):580-9 (1996); Madiyalakan et al., *Hybridoma* 16(1):41-5 (1997); Osterborg et al., *Blood* 91 (7):2459-66 (1998); and Pride et al., *Clinical Cancer Research* 4:2363 (1998)]. It is therefore expected that the immunization of prostate cancer patients with the binding agents of the present invention may also induce a specific and protective CTL immune response against PSA.

This makes PSA an attractive target for immunotherapy. Several attempts at generating an immune response have met with limited success [Xue et al, *The Prostate*, 30:73-78 (1997); Correlae et al, *J. National Cancer Institute*, 89:293-300 (1997); Choe, et al, *Cancer Investigations*, 5:285-291 (1987); Wei, et al, *Cancer Immunol. Immunother.*, 42:362-368 (1996), and International Application No. PCT/US97/04454, filed 19 Mar. 1997]. Combining the profound impact of prostate cancer with the lack of effective therapies, it is clear that alternative modalities of treatment need to be explored and that the ability to elicit a therapeutic immune response to PSA would be highly desirable.

Immunotherapies involve one or more components of the immune system to trigger a complex cascade of biological reactions focused on eliminating a foreign molecule from the host. The immune system consists of a wide range of distinct cell types, the most important of which are the lymphocytes. Lymphocytes determine the specificity of immunity, and it is their response that orchestrates the effector limbs of the immune system. Cells and proteins, such as antibodies, that interact with lymphocytes play critical roles in both the presentation of antigen and in the mediation of immunologic functions.

Individual lymphocytes provide a specialized function by responding to a limited set of structurally related antigens. As noted in more detail below, this function is defined structurally by the presence on the lymphocyte's surface membrane of receptors that are specific for binding sites (determinants or epitopes) on the antigen. Lymphocytes differ from each other not only in the specificity of their receptors, but also in their functions. One class of lymphocytes, B cells, are precursors of antibody-secreting cells, and function as mediators of the humoral immune response. Another class of lymphocytes, T cells, express important regulatory functions, and are mediators of the cellular immune response.

Cancer immunotherapy is based on the principle of inducing the immune system to recognize and eliminate neoplastic cells. The key elements in any immunotherapy is inducing the host immune system to first recognize a molecule as an unwanted target, and then inducing the system to initiate a response against that molecule. In healthy hosts, the immune system recognizes surface features of a molecule that is not a normal constituent of the host (i.e., is "foreign" to the host). Once the recognition function occurs, the host must then direct a response against that particular foreign molecule.

Both the recognition and the response elements of the immune system involve a highly complex cascade of biological reactions. In most immunologically based disorders, at least one of the steps in the recognition phase, or at least one of the steps in the response phase, are disrupted. Virtually any disruption in either of these complex pathways leads to reduced response or to no response. The inability of the immune system to destroy a growing tumor has been attributed, among other factors, to the presence of tumor-associated antigens (TAA) that induce immunological tolerance and/or immunosuppression. For example, in some kinds of cancer, the cancer itself tricks the host into recognizing a foreign cancer cell as a normal constituent, thus disrupting the recognition phase of the immune system. The immunological approach to cancer therapy involves modification of the host-tumor relationship so that the immune system is induced or amplifies its response to the TAAs. If successful, inducing or amplifying the immune system can lead to tumor regression, tumor rejection, and occasionally, to tumor cure.

One of the host system's mechanisms for combating a foreign molecule is called a humoral response, the production of an antibody against a specific foreign molecule (called an antigen). Typically, the antibody's capability of binding the antigen is based on highly complementary structures. That is, the shape of the antibody must contain structures that are the compliment of the structures on the antigen. When the respective structures are fully complimentary, then the two molecules bind tightly.

Antigens are molecules that interact with specific lymphocyte receptors—surface T cell antigen receptors and B cell immunoglobulin receptors. A particular B or T cell binds to a very specific region of the antigen, called an antigenic determinant or epitope. Thus antigens are molecules that bear one or more epitopes which may be recognized by specific receptors in an immune system, a property called antigenicity.

Immunogenicity is the property of stimulating the immune system to generate a specific response. Thus, all immunogens are antigens, but not vice-versa. Although an immune system may recognize an antigen, it does not respond to the antigen unless the antigen is also immunogenic.

An immune response to a particular antigen is greatly influenced by the structure and activity of the antigen itself, as well as myriad other factors. In some cases, the immune system is not able to generate an immune response to a particular antigen, a condition that is called tolerance.

In influencing whether an antigen is immunogenic or immunotolerant, an important characteristic of the antigen is the degree of difference between the antigen and similar molecules within the host. The most immunogenic antigens are those that have no homologs in the host, i.e., those that are most "foreign." Other factors that promote immunogenicity include higher molecular weight, greater molecular complexity, the proper antigen dose range, the route of administration, the age of the host, and the genetic composition of the host.

As noted above, antigens may have one or more epitopes or binding sites that are recognized by specific receptors of the immune system. Epitopes may be formed by the primary structure of a molecule (called a sequential epitope), or may be formed by portions of the molecule separate from the primary structure that juxtapose in the secondary or tertiary structure of the molecule (called a conformational epitope). Some epitopes are hidden in the three dimensional structure of the native antigen, and become immunogenic only after a conformational change in the antigen provides access to the epitope by the specific receptors of the immune system. This is an important feature and function in the ability of a therapeutic reagent to initiate recognition and response to an antigen, the inducing both a cellular and humoral response to the antigen, and to increasing the antigenicity of a molecule without affecting its immunogenicity.

One of the responses generated by the immune system, a humoral response, involves the production of antibodies. Antibodies bear three major categories of antigen-specific determinants—isotypic, allotypic, and idiotypic—each of which is defined by its location on the antibody molecule. For the purpose of the present invention, we shall only focus on the idiotypic category.

Idiotypic determinants, or idiotopes, are markers for the V region of an antibody, a relatively large region that may include several idiotopes each capable of interacting with a different antibody. The set of idiotopes expressed on a single antibody V region constitutes the antibody idiotype. An antibody (Ab1) whose antigen combining site (paratope) interacts with an antigenic determinant on another antibody V region (idiotope) is called an anti-idiotypic antibody (Ab2). Thus, an antibody includes an antigen binding site, and may include one or more antibody binding sites. There are two types of anti-idiotypic antibodies, sometimes called Ab2$\alpha$ and Ab2$\beta$. In one type of anti-idiotype antibody (Ab2$\beta$), the combining site perfectly mimics the structure of the antigen epitope recognized by the Ab1 antibody. This type of anti-idiotype is said to represent the internal image of the antigen. By definition, the antigen and this type of anti-idiotype antibody compete for the same binding site on $Ab_1$, and the antigen inhibits the interaction between Ab1 and the anti-idiotypic antibody. The phenomenon of producing an anti-idiotypic antibody having the internal image of the antigen may permit the use of antibodies to replace the antigen as an immunogen.

The second type of anti-idiotype, Ab2$\alpha$, binds to an idiotope of Ab1 that is distinct from the antigen binding site, and therefore may be characterized in terms of the antigen's inability to prevent the binding of the anti-idiotype to Ab1. For this type of anti-idiotype, Ab1 can bind to both the antigen and the anti-idiotypic antibody. For a graphic representation of these types of antibodies and their interaction, see FIG. 1.

These various interactions based on idiotypic determinants is called the idiotypic network is based on the immunogenicity of the variable regions of immunoglobulin molecules (Ab1) which stimulate the immune system to generate anti-idiotypic antibodies (Ab2), some of which mimic antigenic epitopes ("internal image") of the original antigen. The presence of internal image antibodies (Ab2) in the circulation can in turn induce the production of anti-anti-idiotypic antibodies (Ab3), some of which include structures that react with the original antigen.

In addition to a humoral response, the immune system may also generate a cellular response mediated by activated T-cells. There are a number of intercellular signals important to T cell activation. Under normal circumstances an antigen degrades or is cleaved to form antigen fragments or peptides.

Presentation of antigen fragments to T-cells is the principal function of MHC molecules, and the cells that carry out this function are called antigen-presenting cells (APC: including but not limited to dendritic cells, macrophages, and B cells).

In addition to generating a humoral response, Ab1 and Ab2 have been shown to induce a cellular immune response characterized by proliferative lymphocytes (helper and suppressor lymphocytes), as well as cytotoxic lymphocytes. Therefore, according to the idiotypic network theory, the injection of anti-PSA antibody should result in the induction of a specific cellular and humoral immune response against the PSA molecule. The concept that anti-idiotypic antibodies function as immunogens has been shown by successful immunization against tumoral, bacterial, viral and parasitic antigens in animal models. Generating Ab2 is an indicator of the existence of a robust immune response that inherently reflects the induction of immune system pathways.

The capture and processing of an antigen by APCs is essential for the induction of a specific immune response. The three major APCs are dendritic cells, macrophages and B-lymphocytes; dendritic cells are the most efficient. The injected antibody forms a complex with a circulating PSA, and can be targeted to dendritic cells and macrophages through the Fc-receptors present on these cells. However the high number of Fc receptors on neutrophils may considerably limit this process.

The capture and processing of PSA by B-cells may also occur through the interaction of the membrane bound Ab2 with the anti-PSA/PSA complexes and in a similar manner through the interaction of membrane bound Ab3 with PSA (complexed or not with the anti-PSA antibody).

SUMMARY OF THE INVENTION

The present invention is the use of a monoclonal antibody that specifically binds to a circulating prostate-specific antigen at a binding site that results in the production of anti-anti-idiotypic antibodies. A composition according to the present invention induces both a humoral and cellular immune response to PSA. Furthermore, a composition according to the present invention induces or amplifies antigenicity of a tumor-associated antigen without affecting its immunogenicity.

A method according to the invention preferably comprises introducing a sufficient amount of antibody into a host to stimulate a humoral and cellular immune response. The antibody composition may be formulated with an adjuvant or in a liposomal or micellular formulation.

The antibody according to the present invention is useful in generating a humoral and cellular immune response against PSA in a broad segment of the human population with differing HLA class I molecule types. This is in part due to the antibody's specificity for a particular sequence on the PSA molecule.

This sequence SEQ ID NO: 1 is of particular importance for PSA targeted immunotherapy since it contains consensus amino acid motifs for binding to HLA-A2. Of particular interest is the demonstration that the peptides 141-150, 146-154 and 154-163 can generate in vitro human cytotoxic T-lymphocytes capable of lysing human prostate carcinoma cells. Another important observation is the identification of a cleaved bound at position 145-146 of the clipped form of PSA demonstrating that this sequence is particularly sensitive to proteolytic degradation. The selected anti-PSA antibody may therefore upon binding to PSA protect this particular sequence against proteolytic degradation in the endosomal compartment of APCs and enhance the production of immunogenci peptides capable to induce an anti-PSA immune response.

The accompanying drawings show illustrative embodiments of the invention from which these and other of the objectives, novel features and advantages will be readily apparent.

DESCRIPTION OF THE DRAWINGS

FIG. 10a is for PSA and FIG. 10b is for a PSA peptide.

DETAILED DESCRIPTION OF THE INVENTION

Figures 1, 2:
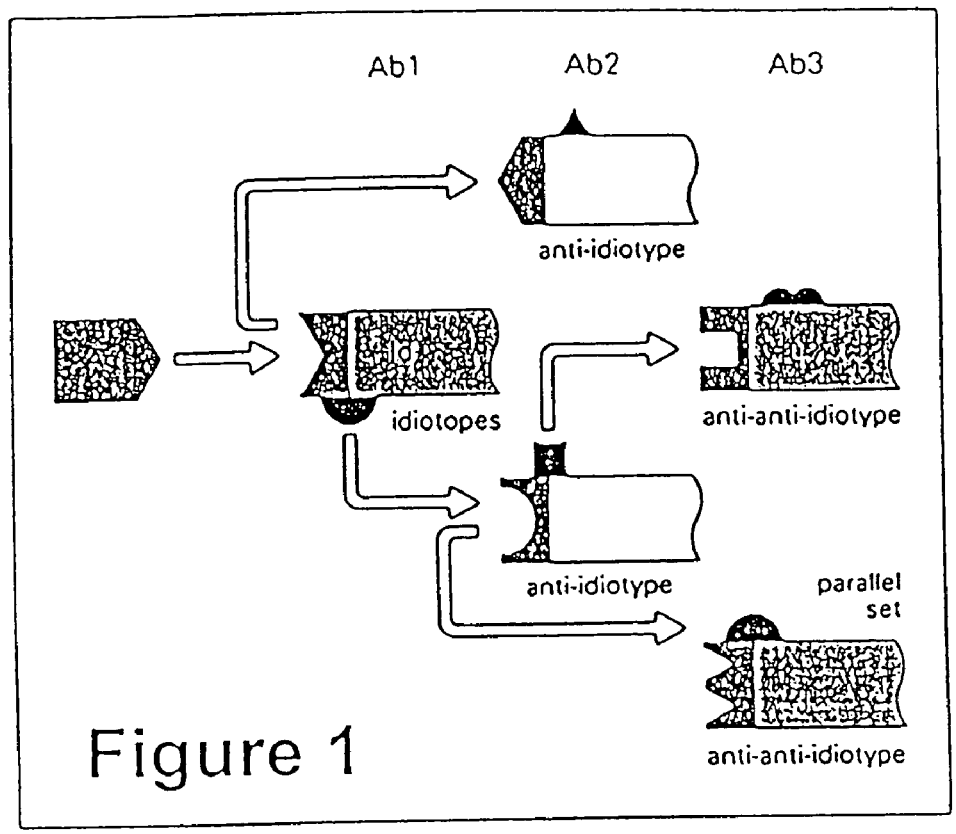
FIG. 1 is a graphic representation of the different types of antibodies and their structural relationship to each other and to an antigen.
FIG. 2 shows the amino acid sequence of a prostate-specific antigen binding site.

The present invention is a composition comprising a binding agent, such as an antibody, that specifically binds to a prostate specific antigen (PSA), preferably circulating PSA, and even more preferably to an epitope of the PSA molecule corresponding to amino acid sequences 139 to 163. In a preferred embodiment of the invention, the binding agent is a monoclonal antibody.

The present invention is a composition and method of treatment in which the composition includes a binding agent, such as an antibody, that can both induce the production of an anti-anti-idiotype antibody, and can bind with circulating PSA to form a target for antigen presenting cells.

The present invention also comprises a method for treating prostate cancer by administering a composition according to the invention.

The present invention also comprises a composition and method for inducing the production of anti-anti-idiotypic antibodies that specifically bind to a prostate specific antigen.

The present invention also includes a kit containing a composition according to the present invention.

In a preferred embodiment of the invention, a composition comprising a pre-determined antibody that specifically binds to a pre-determined tumor associated antigen is used to bind a soluble antigen produced by the tumor. Once the soluble antigen is bound, the immune system recognizes the antigen as "foreign," and mounts an immune response against the antigen or against the binding agent bound to the antigen. Antigens that can be made immunogenic are potentially useful to induce or activate an immune response, leading to therapeutic and possibly prophylactic benefits.

As used herein the term "prostate specific antigen" includes the in vivo, ex vivo, or in vitro native protein, the native protein whether purified from a native source or made by recombinant technology, as well as any polypeptide, mutein or portion derived therefrom that is capable of generating an immune response to a native conformationally correct PSA. For example, one can make conservative amino acid substitutions in the molecule without adversely affecting the ability to generate an antibody that will also recognize native PSA.

The compositions and methods of the present invention involve prostate cancer that produces a soluble multi-epitopic tumor-associated antigen (TAA). As used herein soluble is used to describe any antigen that is detectable in a body fluid, i.e., blood, serum, ascites, saliva, or the like. Prostate cancer shed soluble tumor antigens, e.g., tumor antigens shed into the bloodstream, as opposed to a surface antigen or an intracellular antigen; exhibits a multi-epitopic tumor associated antigen, preferably of protein or glycoprotein (e.g., mucin) nature; and can be found at a concentration in the patient's body fluid more than is normally present in healthy controls and such a high level signifies a poor prognosis for the patient, yet has not initiated an immune response. As is well known by one skilled in the art, one method of determining whether the concentration of the TAA is greater than is predictive of recurrence of the disease is by comparing the patient's concentration to that of a healthy control. If the concentration of the TAA is higher than the healthy control, then the patient's concentration is predictive of poor prognosis of the disease.

A binding agent (BA), as used herein, refers to one member of an immunologic pair, e.g., a binding moiety that is capable of binding to a single epitope expressed on the tumor antigen. Exemplary binding agents include, but are not limited to: monoclonal antibodies ("MAb"); chimeric monoclonal antibodies ("C-MAb"); genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); tumor-binding peptides; humanized antibodies; any of the above joined to a molecule that mediates an effector function; and mimics of any of the above. The antibody may be a polyclonal antibody or a monoclonal antibody. When the subject is a human subject, the antibody may be obtained by immunizing any animal capable of mounting a usable immune response to the antigen, such as a mouse, rat, goat sheep, rabbit or other suitable experimental animal. In the case of a monoclonal antibody, antibody producing cells of the immunized animal may be fused with "immortal" or "immortalized" human or animal cells to obtain a hybridoma which produces the antibody. If desired, the genes encoding one or more of the immunoglobulin chains may be cloned so that the antibody may be produced in different host cells, and if desired, the genes may be mutated so as to alter the sequence and hence the immunological characteristics of the antibody produced.

Fragments, or fragments of binding agents, may be obtained by conventional techniques, such as by proteolytic digestion of the binding agent using pepsin, papain, or the like; or by recombinant DNA techniques in which DNA encoding the desired fragment is cloned and expressed in a variety of hosts. Irradiating any of the foregoing entities, e.g., by ultraviolet light will enhance the immune response to a multi-epitopic antigen under similar conditions. In a preferred embodiment of the invention, effector functions that mediate CDC or ADCC are not required.

The present invention includes substitutions and deletions within the amino acid structure of the antibody provided that the modifications result in a functionally equivalent antibody with enhanced immunogenicity.

In an embodiment of the invention, a composition includes an antibody that specifically binds to circulating prostate-specific antigen. In an embodiment of the invention, the antibody binds to an epitope of PSA corresponding to amino acid sequences 139-163 of the PSA molecule. More specifically, the antibody binds to a epitope corresponding to the following amino acids: EEFLTPKKLQCVDLHVISNDVCAQV (SEQ ID NO. 1). In a most preferred embodiment, a binding agent according to the invention binds to an epitope of PSA corresponding to amino acid sequences 135 to 150 of the PSA molecule. In accordance with the present invention, other binding agents may be useful in the practice of this invention. For example, other suitable binding agents, such as monoclonal antibodies, include those that bind near the N-terminus of the PSA molecule.

The antibody of the present invention may be formulated into a pharmaceutical composition in combination with a pharmaceutically acceptable carrier for use as an immunogen in a mammal, preferably a human or primate. The composition may further comprise one or more other constituents to enhance the immune response which include but are not limited to biological response modifiers such as dendritic cell growth factors, such as Flt 3; interleukin 2, interleukin 6, interleukin 12, interferon, tumor necrosis factor, GM-CSF and cyclophosphamide. The composition may also comprise at least one HLA class I molecule, or a cell expressing at least one HLA class I molecule in combination with one or more antibodies or fragments thereof. Adjuvants include, for example, RIBI Detox, QS21, alum and incomplete Freund's adjuvant. Liposomal formulations can also be used.

The composition may include one or more adjuvants, one or more carriers, one or more excipients, one or more stabilizers, one or more imaging reagents, and/or physiologically acceptable saline. Generally, adjuvants are substances mixed with an immunogen in order to elicit a more marked immune response. Control vaccinations without the adjuvant resulted in humoral immune responses. The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile and free of undesirable particulate matter. The compositions may be sterilized by conventional sterilization techniques.

A composition according to the invention may be administered to a mammal in an amount effective in generating a PSA specific humoral and cellular immune response. The efficacy of the antibody as an immunogen may be determined by in vivo or in vitro parameters as are known in the art. These parameters include but are not limited to antigen specific cytotoxicity assays, regression of PSA$^+$ tumors, inhibition of PSA$^+$ cancer cells, production of cytokines and the like.

As used herein, "administering" refers to any action that results in exposing or contacting a binding agent, such as an antibody, with a pre-determined antigen, cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention.

In accordance with a method of the invention, the binding agent must be capable of binding a pre-determined binding site or receptor, and may be administered to the patient by any immunologically suitable route. For example, the binding agent may be introduced into the patient by an intravenous, subcutaneous, intraperitoneal, intrathecal, intravesical, intradermal, intramuscular, or intralymphatic routes. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The clinician may compare the anti-idiotypic and anti-isotypic responses associated with these different routes in determining the most effective route of administration. The invention should not be limited to any particular method of introducing the binding agent into the patient.

In accordance with the methods of the present invention, a composition comprising the binding agent may be administered in an amount sufficient to recognize and bind the prostate tumor associated antigen. In a preferred embodiment of the invention, the dosage is sufficient to generate or elicit an immune response against the TAA. An immunologically or therapeutically effective or acceptable amount of binding agent is an amount sufficient to bind a pre-determined antigen in vivo or ex vivo, and is capable of eliciting an immune response to the antigen. The response inhibits or kills tumor cells that carry and present a newly accessible epitope, thereby ameliorating or eliminating the disease or condition that produces the antigen. The immune response may take the form of a humoral response, a cell-mediated response, or both. In a preferred embodiment of the invention, the dosage of the monoclonal antibody is less than the dosage required to elicit ADCC or CDC.

The concentration or dosage of the protein in the composition can vary widely, e.g., from less than about 0.01% to about 15 to 20% by weight. As noted above, the composition is administered in an amount sufficient to stimulate an immune response against the antigen. Amounts effective for this use will depend in part on the severity of the disease and the status of the patient's immune system. Generally, the composition will include about 0.1 µg to about 2 mg or more of protein agent per kilogram of body weight, more commonly dosages of about 1 µg to about 200 µg per kilogram of body weight. The concentration will usually be at least 0.5%; any amount may be selected primarily based on fluid volume, viscosity, antigenicity, etc., in accordance with the particular mode of administration.

Administration may be more than once, preferably three times over a prolonged period. As the compositions of this invention may be used for patient's in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982).

Administration may also include ex vivo administration protocols, e.g., removing a portion of a patient's body fluid, contacting in vitro the body fluid with the therapeutic composition, and then returning the treated body fluid to the patient.

A binding agent may be administered in combination with other binding agents, or may be administered in combination with other treatment protocols or agents, e.g., chemotherapeutic agents.

The therapeutic efficacy of the administered anti-PSA antibody is believed to depend on two different mechanisms of action, although the invention is not to be restricted to the recited mechanisms. The first mechanism is the induction of a specific immunity (humoral immunity) to PSA via the idiotypic network. The second mechanism involves cellular immunity—the administered anti-PSA antibody binds to circulating PSA to form a complex suitable for binding antigen presenting cells (APCs). Of particular interest, this mechanism of action generates a multi-epitopic immune response against the PSA. The targeting of Ar 47.47 at the tumor site upon i.v. injection may also favor the migration and accumulation of immunocompetent cells at the tumor site. The secretion of cytokines by these immune cells may in turn stimulate the production of a protective immune response against various tumor antigens.

In accordance with another embodiment of the invention, the structure of the antibody may be modified in order to enhance its capture by dendritic cells. Exemplary modifications include but are not limited to mannosylation of the anti-PSA antibody or conjugation to an antibody specifically directed against a murine dendritic cell surface market. Unlike the Fc receptors, the mannose receptor is recycled to the cell surface after endocytosis and can therefore allows internalization of ligands in successive rounds. Indeed, mannosylated proteins are presented with 100-fold higher efficiency than un-glycosylated proteins by dendritic cells.

EXAMPLES

Example 1

Production of AR47.47

Figure 3:
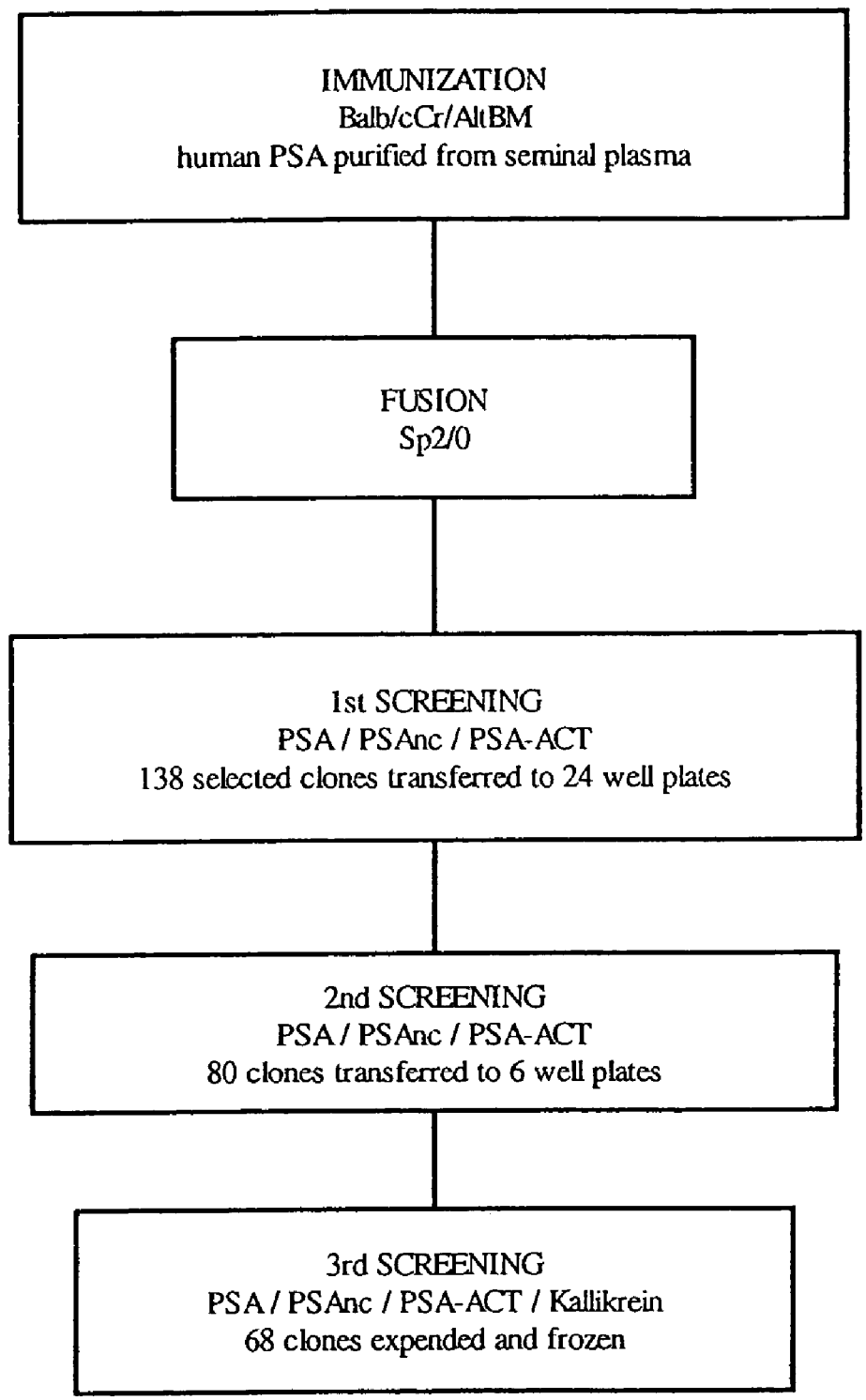
FIG. 3 is a flow chart of the scheme for producing antibodies according to the invention.

Hybridoma clones secreting anti-PSA antibodies were produced by fusion of the murine myeloma cells Sp2/O with the splenocytes of a Balb/c mouse immunized with human PSA (FIG. 3).

Immunogen: PSA purified from human seminal plasma was obtained from Scripps Laboratories, San Diego, Calif. [Cat # P0723 (purity, about 50%); Cat # P0725 (purity, 99%)].

Mice: Male Balb/cCr/AltBM mice, 6 weeks of age, were purchased from Jackson Laboratories and housed on 7th floor Dentistry/Pharmacy Building (HSLAS facilities).

Immunization protocol: Mice were immunized i.p. with 30 µg of PSA (Cat # P0723) in complete Freund adjuvant. The mice received subsequently two i.p. injections at 10 days interval with 30 µg of PSA (Cat # P0723). The first booster was performed in incomplete Freund adjuvant whereas the 2nd booster was performed in PBS. The serum levels of anti-PSA antibodies were measured by ELISA on PSA coated plates (ELISA # 1) and the mouse with the higher serum level was subjected to a final intra-splenic boost with 30 µg of PSA (Cat # P0725) in PBS.

Fusion: 3 days after the final intra-splenic boost the hybridomas were generated by fusion of spleen cells with the murine myeloma cell line Sp2/0-Ag14 (ATCC CRL-1581).

Screening:

First screening: Hybridoma clones secreting anti-PSA antibodies were first detected by ELISA on PSA coated plates (ELISA #1). We selected 80 positive clones from this first screening. Those clones are currently kept frozen in liquid nitrogen tank.

Second screening: The positive clones were further screened against PSA complexed to alpha anti-chymotrypsin (PSA-ACT) (ELISA #2); PSA non complexing to alpha anti-chymotrypsin (ELISA #4); Plasmatique kallikrein (ELISA #5); and PSA peptide 139-163 (ELISA #6)

The reactivity of the AR47 clones towards the different forms of PSA and towards kallikrein is reported in Example 2. The isotype of the antibodies secreted by AR47 clones is reported in Example 3.

The criteria of selection of a clone for additional studies was based on the reactivity towards PSA and PSA-ACT (the two main forms of immunoreactive PSA in human serum), the reactivity towards PSA peptide 139-163 (PSA sequence involved in cellular immunity), and the isotype of the secreted antibodies. Based on these criteria, the hybridoma clone AR47.47 was selected.

Adaptation from HAT Medium to Standard Medium:

AR47 clones arising from 96 well plates and grown in HAT medium were first transferred into 24 well plates containing 2 ml of HT medium/well and then, once confluence was reached, transferred into 6 well plates containing 6 ml of HT medium/well. The adaptation of the cells from HT medium to standard medium was performed gradually.

HAT medium: RPMI 1640, 10% FBS, HAT supplement, OPI supplement, 0.3 ml/ml glutamine, 100 µg/ml streptomycin, 100 U/ml penicillin HT medium: RPMI 1640, 10% FBS, HT supplement, OPI supplement, 0.3 mg/ml glutamine, 100 µg/ml streptomycin, 100 U/ml penicillin Standard medium: RPMI 1640, 10% FBS, 0.3 mg/ml glutamine, 100 µg/ml streptomycin, 100 U/ml penicillin.

Ascites can be produced in mice pre-treated with pristane (0.5 ml/mouse) and injected with AR47.47R6R6. The concentration of AR47.47 in ascites was calculated to be in the range of 4 to 6 mg/ml.

| # of mice | # of cells injected per mouse | total # of tapping | total vol. of ascites collected |
|---|---|---|---|
| 4 | $1.8 \times 10^6$ | 10 | 26 ml |
| 5 | $1.8 \times 10^6$ | 19 | 48 ml |
| 3 | $2 \times 10^6$ | 10 | 18 ml |
| 5 | $1.9 \times 10^6$ | 15 | 29 ml |

Prostate specific antigen (PSA) represents an attractive target for the immunotherapy of prostate cancer. This glycoprotein is almost exclusively synthesized by the prostatic gland and is currently used for the diagnosis and monitoring of prostate cancer patients. However, since PSA is recognized as a self-antigen, it is essential for effective immunotherapy to develop innovative strategies capable of triggering the immune system and induce a protective immunity against PSA expressing cells. This example demonstrates the use of an antibody to elicit an anti-idiotype cascade associated with an antigen specific anti-tumor immune response. A large panel of anti-PSA monoclonal antibodies have been produced in our laboratory and these antibodies were evaluated for their potential therapeutic efficacy against prostate cancer. We have demonstrated that the immunization of mice with a selected anti-PSA antibody can induce a specific immunity against PSA itself. These results therefore emphasize the potential use of anti-PSA antibodies for the immunotherapy of prostate cancer.

Hybridoma clones secreting anti-PSA antibodies were produced by fusion of the murine myeloma cells Sp2/O with the splenocytes of a Balb/c mouse immunized with human PSA. An exemplary clone, AR47.47, binds to an epitope of PSA corresponding to amino acid sequences I39-I63 of the PSA molecule. It has now been shown that AR 47.47 also recognizes amino acid sequences I35-I50, produces a stronger signal, and may be the minimum sequences required for binding.

The hybridoma clone AR47.47 was deposited on Apr. 29, 1998 with the American Type Culture Collection (ATCC), located at 10801 University Blvd., Manassas, Va. 20110-2209, in accordance with the Budapest Treaty. The AR47.47 hybridoma clone was assigned the ATCC designation number HB-12526.

The first criteria of selection used to identify the anti-PSA antibody was the ability of this antibody to interact with circulating PSA. Circulating PSA is found either in a free form or complexed to anti-proteases such as α-anti-chymotrypsin and α2-macroglobulin. To screen for clones we used three different forms of PSA: free PSA; PSA complexed to α-anti-chymotrypsin (PSA-ACT); and free PSA non complexing to α-anti-chymotrypsin (PSA-nc). Free PSA corresponds to PSA directly purified from human seminal fluid. Co-incubating free PSA with purified ACT results in the formation of PSA-ACT and PSA-nc. PSA-nc can be separated by gel filtration chromatography. It is believed that PSA-nc may represent the free form of PSA present in the circulation. Complexing of PSA with α2-macroglobulin results in the total encapsulation of PSA. As a consequence, this form of PSA is no longer detectable by monoclonal anti-PSA antibodies. We therefore did not use this form of circulating PSA for the screening.

PSA belongs to the kallikrein family and a high degree of structural homology is found between PSA and the kallikreins HKl and HK2. The absence of cross reactivity of the anti-PSA antibody with kallikrein isolated from human plasma was used as second criteria for selection.

The hybridoma clone AR47.47 responded to the criteria described above, a strong immunoreactivity was observed with the three forms of PSA used for the screening whereas no cross reactivity was observed with human plasmatic kallikrein. The hybridoma clone AR47.47 was cloned twice by limiting dilution and the second generation clone AR47.47R6R6 was chosen for further studies. Clone AR47.47R6R6 was adapted to standard medium (RPMI 10% FBS) and a cell bank was formed. The absence of mycoplasma contamination was verified by using the Boehringer Manheim mycoplasma test. Clone AR47.47R6R6 has been deposited in the American Type Culture Collection, and has received Accession No. H-B 12526.

Immunization in DBA mice with a binding composition according to the invention (AR47.47) was examined for the induction of a specific PSA immunity via the idiotypic network (i.e. induction of Ab3 antibodies). Anti-PSA antibodies (Ab3) could be detected in the serum of animals immunized with AR 47.47, a minimum of two injections of AR 47.47 was required for Ab3 production. No reactivity towards PSA was detected for the control groups (mice immunized with an isotype matched control antibody not related to PSA and mice receiving PBS injections).

AR 47.47 is directed towards a PSA epitope comprised between the sequence I39-I63 of the PSA molecule. The anti-PSA antibodies produced by AR 47.47 immunized mice can specifically interact with the PSA peptide I39-I 63, showing that at least part of the Ab3 produced are identical in term of specificity to AR 47.47. These results demonstrate that the immunization with AR 47.47 can induce a specific anti-PSA immunity in the host.

Example 2

Clone Culture and Productivity

Growth Characteristics in Standard Medium

Figure 4A:
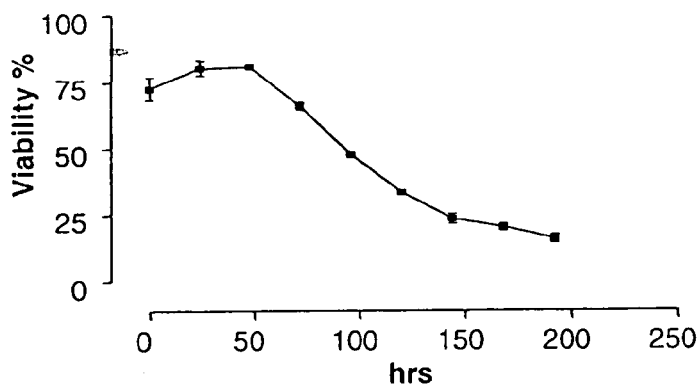
FIGS. 4A-4C show the growth characteristics of an antibody according to the invention.
Figure 4B:
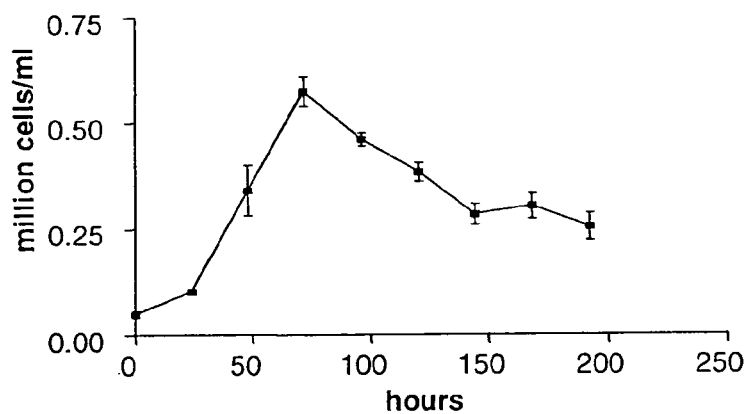
Figure 4C:
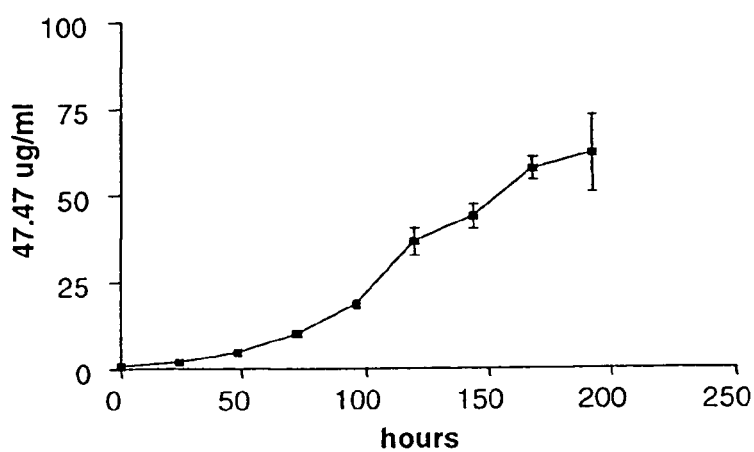

Using standard medium (RPMI 1640, 10% FBS, 0.3 mg/ml glutamine, 100 µg/ml streptomycin, 100 U/ml penicillin), AR47.47R6R6 hybridoma cells were seeded at $5 \times 10^4$ cells/ml in 6 well plates and cultured for several days. Each day the cell concentration was defined by counting the cells manually with an hematocytometer, the cell viability was determined by trypan blue exclusion, and the antibody concentration in the culture media was measured by ELISA (ELISA # 8). Three independent experiments were performed. The growth characteristics of the AR47.47R6R6 hybridoma clone are shown in FIG. 4 and the following table:

|  | Exp. #1<br>FBS Lot #1 | Exp. #2<br>FBS Lot #1 | Exp. #3<br>FBS Lot #2 |
| --- | --- | --- | --- |
| Maximum cell concentration (million viable cells/ml) | 0.63 | 0.66 | 0.61 |
| Maximum viability (%) | 83 | 89 | 92 |
| generation time (hr) | 19.5 | 21.9 | 26.4 |
| Maximum MAb secretion (µg/ml) | 65 | 61.3 | 57.4 |

The AR47.47R6R6 clone has a generation time of 22 hours and can grow to a maximum of 0.6 millions cells/ml. Highest antibody level in the culture media was calculated to be approximately 60 µg/ml.

AR47.47 hybridoma cells were adapted to serum free medium (SFM, Gibco) and protein free medium (UltraDOMA-PF, Biowhitaker). AR47.47R6R6 hybridoma cells were adapted to serum free medium (SFM, Gibco, cat # 12045-084) and protein free media (UltraDOMA-PF, Bio Whittaker, cat #15-7-27 and 08-242F). AR47.47R6R6 was easily adapted to the protein free medium UltraDOMA. In this medium, the cells were best maintained when seeded at a concentration lower than 0.1 millions cells/ml.

The growth characteristics of AR47.47R6R6 in standard media (RPMI 10 % FBS), in RPMI 5% FBS, and in Ultra-DOMA are compared in the following table:

|  | RPMI 10% | RPMI 5% | UltraDOMA |
| --- | --- | --- | --- |
| Maximum viable cells per ml | 0.6 million cells/ml | 0.6 million cells/ml | 0.3 million cells/ml |
| generation time | 19.55 hours (Exp #1)<br>21.9 hours (Exp #2)<br>26.4 hours (Exp #3) | 17 hours | 18 hours (Exp #1)<br>27.5 hours (Exp #2) |
| Maximum antibody concentration | 65 µg/ml on day 8 | 60 µg/ml on day 8 | 10 µg/ml (day 6, Exp #1)<br>18 µg/ml (day 8, Exp #2) |

The adaptation of AR47.47R6R6 to serum free medium (SFM, Gibco) was in contrast considerably more difficult. The cells did not survived if diluted at a concentration lower than $1 \times 10^5$ cells/ml. The cells were best maintained at a cell concentration comprised between $2-4 \times 10^5$ cells/ml. The growth characteristics in this medium were not studied.

Example 3

AR 47.47 was purified by affinity chromatography from either ascites or from cell culture medium. The affinity column used is the Gamma Bind Plus Sepharose from Pharmacia Biotech. The purification of the antibody was performed according to the manufacturer instruction protocol. The chromatography was monitored by measuring the absorbency at 280 nm (total protein concentration) and by testing the different fractions for the presence of anti-PSA antibody (ELISA # 1). The fractions containing purified antibody were concentrated and dialyzed against PBS. The purity of the antibody was analyzed by SDS-PAGE. The concentration of the antibody in the starting materials and in the purified fractions was determined by ELISA (ELISA # 8) and by measuring the absorbency at 280 nm (the conversion of the absorbency value to a concentration value was made using an $\epsilon=1.46$).

Figure 5A:
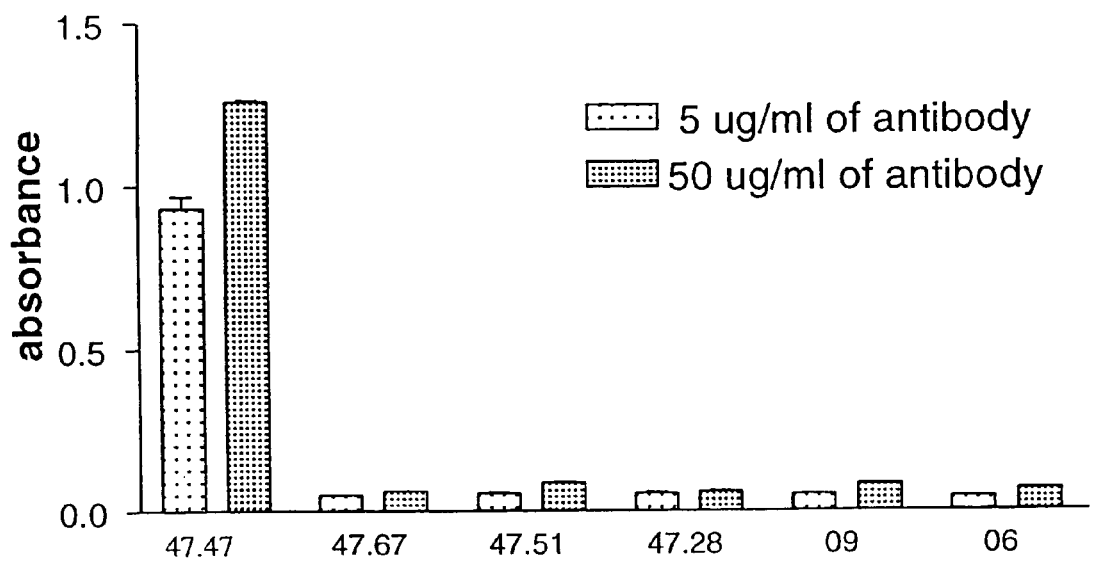
FIGS. 5A-5B show the binding characteristics of an antibody according the to the invention.
Figure 5B:
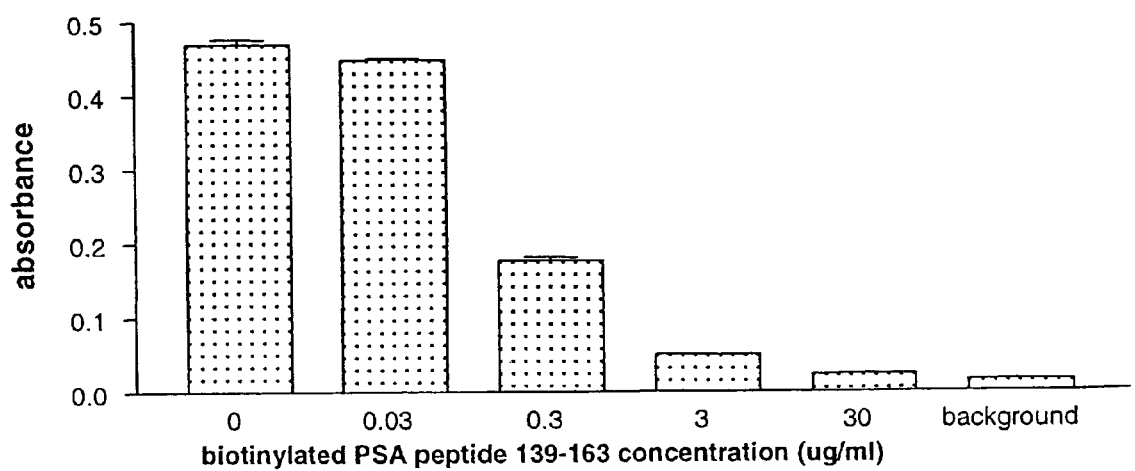

AR47.47 is an IgG1 antibody and interacts specifically with free PSA as well as with PSA complexed with ACT. Synthetic linear PSA peptides were used to identify the epitope recognized by AR47.47 (FIG. 5). Direct binding as well as competitive experiments demonstrate that the epitope recognized by AR47.47R6R6 is comprised between the PSA sequence 139-163. AR47.47 does not recognize human plasmatic kallikrein. The isotype of AR47.47R6R6 was determined in an ELISA kit (Southern Biotechnology), and is a murine IgG1,k antibody. AR47 antibodies specifically recognize PSA, PSA-ACT, and PSAnc.

The domain of the PSA molecule comprised between the sequence 140-163 is of particular interest for the development of an immunotherapeutic product for prostate cancer. Indeed, the following PSA peptides; 141-150, 146-154, 154-163, bind to HLA-A2 molecules and cytotoxic T lymphocytes specific for these peptides have been generated in vitro.

Using a direct binding assay with the N-biotinylated PSA peptide 139-163, we have demonstrated that AR47.47 is specifically directed against this sequence (ELISA #5). Only AR47.47 binds to the PSA peptide 139-163. The specificity of AR 47.47 for the PSA sequence 139-163 was further confirmed by a competitive binding assay (ELISA # 7). The binding of AR47.47 to immobilized PSA can be inhibited in a dose dependent manner by N-biotinylated PSA peptide 139-163. In an attempt to identify more precisely the minimal sequence recognized by AR 47.47, we have studied, using the same competitive assay (ELISA # 7), the inhibition of the binding of AR47.47 to PSA by the PSA peptides 141-150, 146-154, 154-163:

| | |
| --- | --- |
| PSA 139-163 | EEFLTPKKLQCVDLHVISNDVAQV (SEQ ID NO: 1) |
| PSA 141-150 | FLTPKKLQCV (SEQ ID NO: 2) |
| PSA 146-154 | KLQCVDLHV (SEQ ID NO: 3) |
| PSA 154-163 | VISNDVCAQV (SEQ ID NO: 4) |

The 9 amino-acid short peptide sequences were not able to inhibit the binding of AR 47.47 to PSA. The absence of inhibition can be explained by AR 47.47 recognizing a conformational epitope, and/or AR 47.47 recognizing a linear epitope but the peptide sequences used are not representative of the minimal binding sequence of AR 47.47 for PSA (for example AR 47.47 may recognizes the region 139-148 of the PSA molecule). It is worth mentioning that all the peptide sequences used possess a cysteine. It is likely that the peptides will dimerize immediately after solubilization by formation of a disulfide bridge between two cysteine residues. The dimerized peptides may not be recognized by AR47.47. It has been shown, however, that various antibodies recognize an epitope near the N-terminus of the PSA molecule, and these antibodies induce a therapeutically beneficial immune response.

The measurement of the affinity of AR 47.47 for PSA was determined using either radiolabeled AR 47.47 (RIA # 1) either radiolabeled PSA (RIA # 2). The Kd values calculated from independent experiments are reported in the following table:

| Radiolabeled ligand | Specific activity (μCi/μg) | affinity for PSA Kd (nM) | affinity for PSA-ACT Kd (nM) | affinity for PSA peptide Kd (nM) |
|---|---|---|---|---|
| AR 47.47 | 47 μCi/μg | 2.1 | 1.6 | |
| | | 2 | 1 | |
| AR 47.47 | 15.8 μCi/μg | 3.3 | | 3.4 |
| AR 47.47 | 29 μCi/μg | 2.77 | | 2.3 |
| | | 2.2 | | 1.6 |
| PSA | 7.65 μCi/μg | 1.1 | | |
| PSA | 7.65 μCi/μg | 0.6 | | |

The PSA sequence recognized by AR 47.47 does not contain tyrosine and therefore is likely not to be affected by the iodination process. The slightly higher affinity of AR 47.47 calculated when radiolabeled PSA is used in comparison of radiolabeled AR 47.47 may suggest that the affinity of the antibody is slightly diminished by the iodination process.

The affinity of AR 47.47 for PSA-ACT was performed using radiolabeled AR 47.47 (RIA #3). Two independent experiments were performed. The affinity constants calculated from the Scatchard plots were 1.6 nM and 1 nM respectively. The affinity of AR47.47 for both PSA and PSA-ACT therefore appears to be close.

The affinity of AR 47.47 for PSA peptide 139-166 was performed using radiolabeled AR 47.47 (RIA #4). Three independent experiments were performed. The affinity constants calculated from the Scatchard plots demonstrate similar affinity of AR 47.47 for both PSA and PSA peptide 139-163.

| Source | MAb concentration in the starting materials | Total amount of antibody purified | Yield |
|---|---|---|---|
| ascites (9.5 ml) | 4 mg/ml | 31 mg | 80% |
| ascites (56 ml) | 4.4 mg/ml | 145 mg | 60% |
| culture medium (120 ml) | 14.6 mg/ml | 1.4 mg | 80% |

The fragmentation of AR47.47R6R6 antibody into F(ab)2 fragments was realized by enzymatic digestion using immobilized ficin (Pierce) as described by the manufacturer instructions. The separation of the Fab fragments from the Fc fragments was performed by affinity chromatography on Protein A column. The non-bound fractions washed out of the column contain the fab fragments whereas the bound fractions contained the Fc fragment and eventually the remaining non-digested antibody.

The fractions eluted from the Protein A column were first tested for their immunoreactivities with anti-Fc and anti-Fab antibodies (ELISA # 9 and 10). The results obtained indicate that the first fractions directly eluted from the column contain as expected Fab [either Fab or F(ab)2] fragments and were not contaminated with Fc fragments. We further demonstrated that these Fab fragments were still able to bind PSA (ELISA # 11, RIA #5).:SDS PAGE analysis of AR 47.47 purified from GammaBind+column.

Example 4

Animal Model

Figure 6:
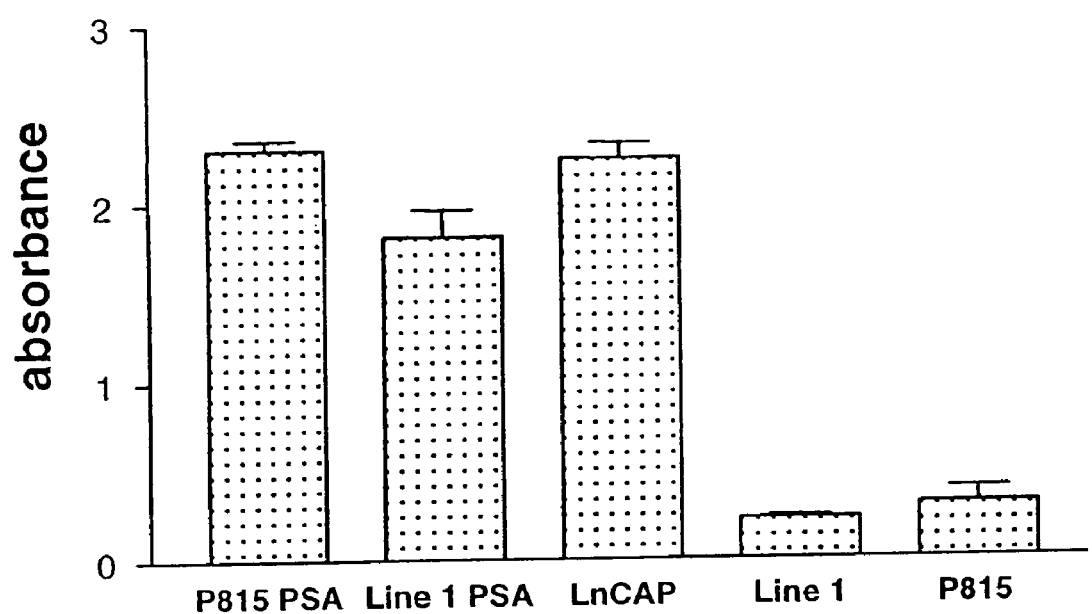

Two murine PSA-transfected cell lines (Line-1-PSA; P815-PSA) were obtained from Dr. E. M. Lord (University of Rochester, N.Y.). Line-1 is a Balb/cByJ (H-$2^d$) mouse lung carcinoma cell line and P815 is a DBA/2 (H-$2^d$) mastocytoma cell line. The transfected cell lines Line-1-PSA and P815-PSA are stably transfected and secrete high level of PSA in the culture medium (FIG. 6). The levels of PSA expression by these transfected cell lines is comparable to what has been observed in the dihydrotestosterone-induced human prostate cell line LnCAP [Wei et al; *Cancer Immunol Immunother,* 42:362-368 (1996)].

The expression of MHC class I and MHC class II molecules was studied by FACS analysis using the commercially available antibodies directed against H-2KdDd (MHC class I) and I-Ad (MHC class II). P815-PSA cells grown in vitro or isolated from solid tumor (from DBA mouse) express high level of MHC class I molecules but only low levels of MHC class II molecules. When grown in vitro, Line 1-PSA expressed very low levels of MHC class I and II molecules. However, the expression of MHC class I and II molecules could be induced by treatment of the cells for 5 days with 3% DMSO.

| | MHC Class I | | MHC Class II | |
|---|---|---|---|---|
| | negative control (mean) | MAb anti-H2K$^d$d$^d$ (mean) | negative control (mean) | MAb anti-I-A$^d$ (mean) |
| P815-PSA | | | | |
| grown in vitro | 3 | 652 | 4 | 41 |
| isolated from solid tumor | 3 | 849 | 3 | 69 |
| Line 1-PSA | | | | |
| grown in vitro | 4 | 18 | 15 | 46 |
| isolated from solid tumor | 5 | 91 | 18 | 113 |

Two syngeneic tumor models were established. The first animal model consists of Balb/cByJ mice injected intravenously with 0.1 million Line-1-PSA tumor cells. After 3-4 weeks the mice were sacrificed and the tumor burden was calculated by measuring the number of tumor foci in the lung and by measuring the weight of the lungs.

The second animal model consists of DBA/2 mice injected subcutaneously with 0.5 million P815-PSA cells. After 2 weeks the tumors were palpable and measured at regular intervals with a caliper. Four weeks after the inoculation of the tumor cells, the mice were sacrificed, the tumors are dissected and weighed.

Example 5

Anti-Idiotypic Induction of PSA Immunity in Mice

Mice were used to determine whether immunization with anti-PSA antibodies can induce a specific immunity against PSA via activation of the idiotypic network. The goal of this experiment was to demonstrate that the immunization of mice with anti-PSA antibodies (AbI) can stimulate the immune system to generate anti-idiotypic antibodies (Ab2=surrogate antigen), and anti- anti-idiotypic antibodies (Ab3) capable of reacting with the original antigen.

These experiments used a commercially available antibody as a model anti-PSA antibody (RLSD09; ATCC HB-8525). The purified antibody was conjugated to Keyhole Limpet Hemocyanin (KLH) to enhance its immunogenicity. The anti-PSA antibodies conjugated to KLH were still capable of binding to PSA, indicating that the idiotype of the antibodies were not masked by the conjugation procedure. B43.I3 antibody, a mouse monoclonal antibody of the same isotype as the PSA antibody (IgGI) was used as the control. B43.I3 antibody is specifically directed against the CAI25 ovarian tumor antigen and does not cross react with PSA. In addition FACS analysis verified that the B43.I3 antibody does not bind at the cell surface of Line-I-PSA or P8I 5-PSA.

Mice were subdivided into three groups of five mice each. The first group of mice was immunized with anti-PSA antibody conjugated to KLH. The second group of mice was immunized with the control B43.I3 antibody conjugated to KLH. The third group of mice received PBS injection. Injections were performed i.p. at I0 days intervals with complete Freund adjuvant for the first injection and incomplete Freund adjuvant for the second injection.

Figure 7A:
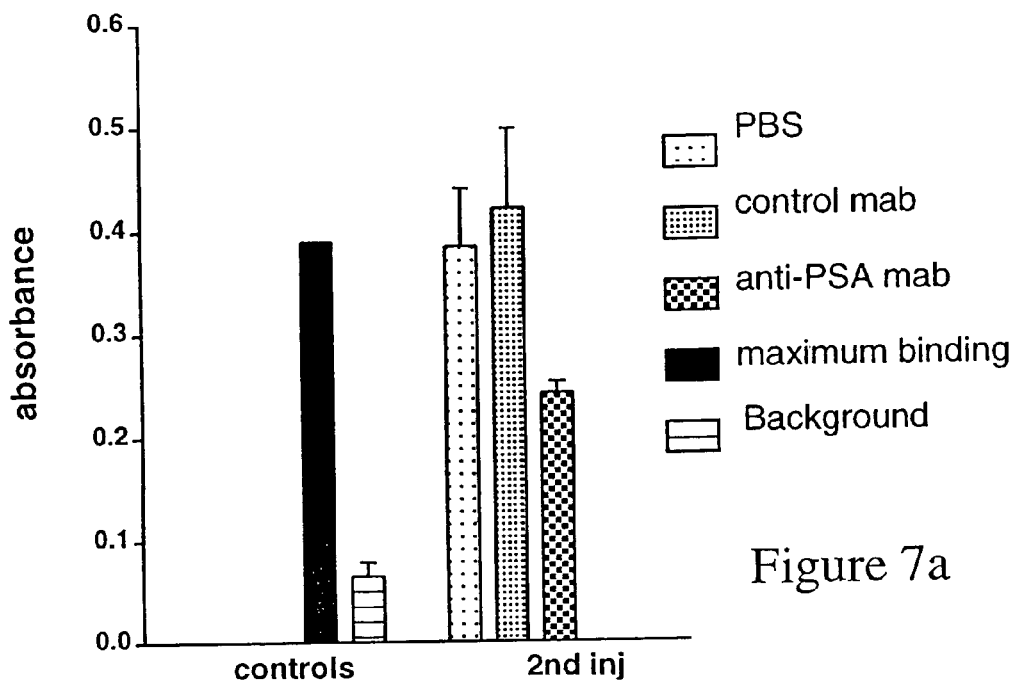
FIGS. 7A-7B show that BALB/c mice (FIG. 7a) and DBA mice (FIG. 7b) immunized with an anti-PSA antibody of the invention, induce the production of anti-idiotype antibodies.
Figure 7B:
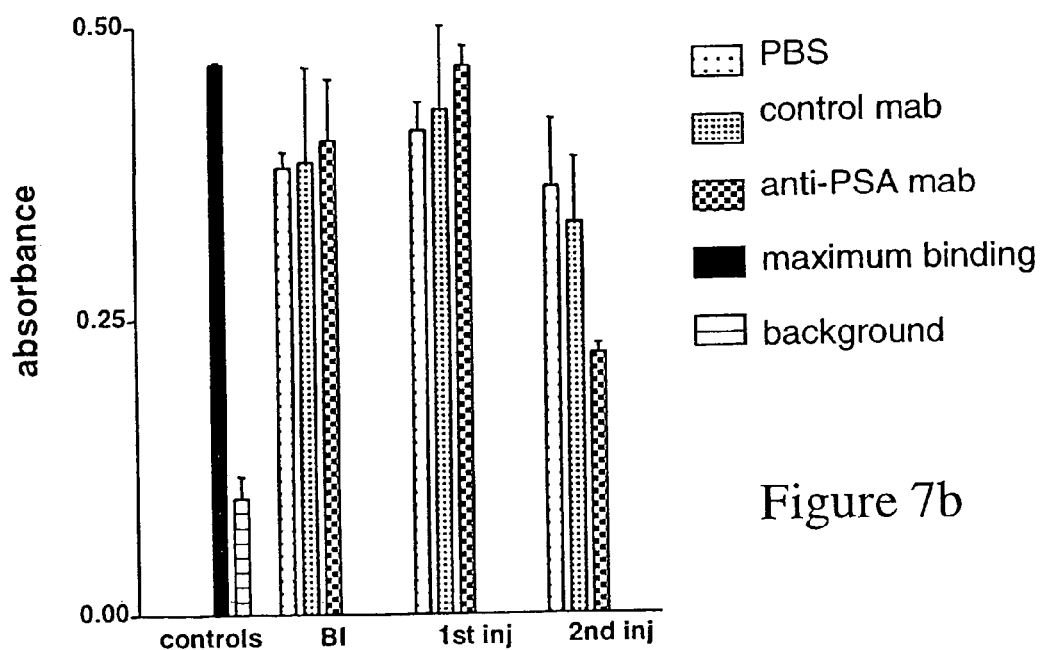

Ab2 is a surrogate antigen capable of mimicking the PSA epitope recognized by the injected anti-PSA antibody. A competitive inhibition assay was established to measure the serum level of Ab2. This assay was performed 5 days after the second injection. An inhibition was observed after incubation in the presence of mouse sera from mice immunized with anti-PSA antibody, but not when sera from mice immunized with control antibody or PBS were used. These results indicate that the immunization of Balb/c mice (FIG. 7A) and DBA mice (FIG. 7B) with the anti-PSA antibody can induce the formation of anti-idiotypic antibody (Ab2) capable of mimicking PSA.

Example 6

Figure 8A:
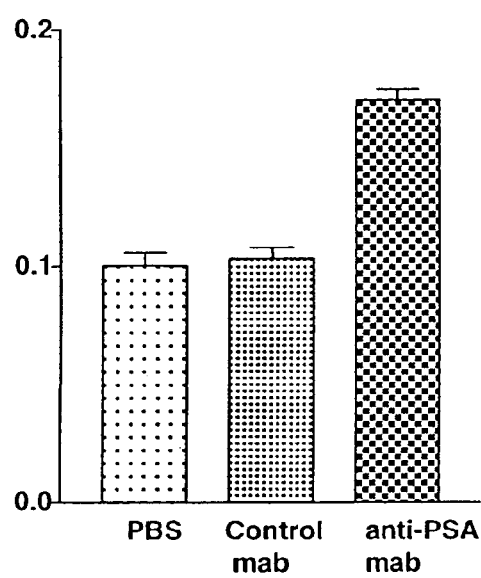
FIGS. 8A-8B show that immunization with an anti-PSA antibody of the invention induces the production of Ab3 antibodies.
Figure 8B:
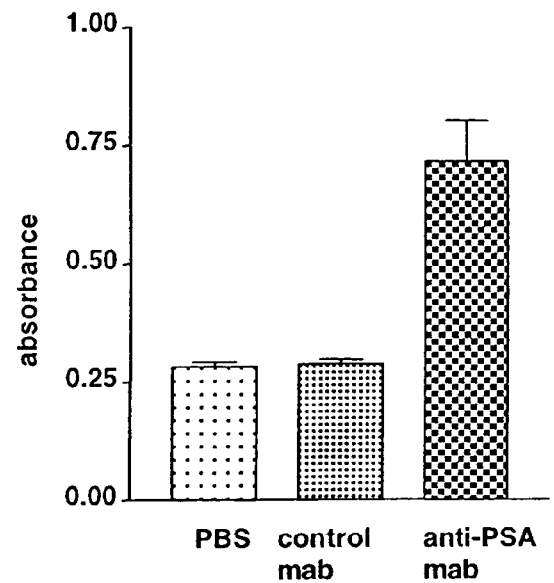

Ab3 corresponds to the anti-PSA antibodies produced by the host. The Ab3 level in the mouse serum was measured by ELISA on PSA coated plate, performed 5 days after the second injection (FIGS. 8A-8B). The anti-PSA antibodies measured by this assay can not correspond to the injected antibodies. Anti-PSA antibodies could be detected in the mouse serum of DBA mice and Balb/c mice immunized with anti-PSA antibody. These results demonstrate that an anti-PSA immune response can be induced in mice by immunization with an anti-PSA monoclonal antibody.

Example 7

Effect of Anti-PSA Immunization on Tumor Development

Balb/c mice were used to determine whether immunization with anti-PSA antibodies can protect the animals against a subsequent tumor challenge. Balb/c mice were divided into 3 groups of 5 mice each. The first group was immunized with anti-PSA antibody RLSD09 conjugated to KLH, the second group was immunized with control antibody B43 conjugated with KLH, the third group received PBS injections. A total of 4 injections were given for each group using 50 µg of antibodies for each injection. The tumor cells Line-1-PSA were injected intravenously between the third and fourth injections. Nineteen days after tumor inoculation, the mice were sacrificed, the number of tumor foci in the lungs and Ab3 levels in the serum were determined.

Figure 9A:
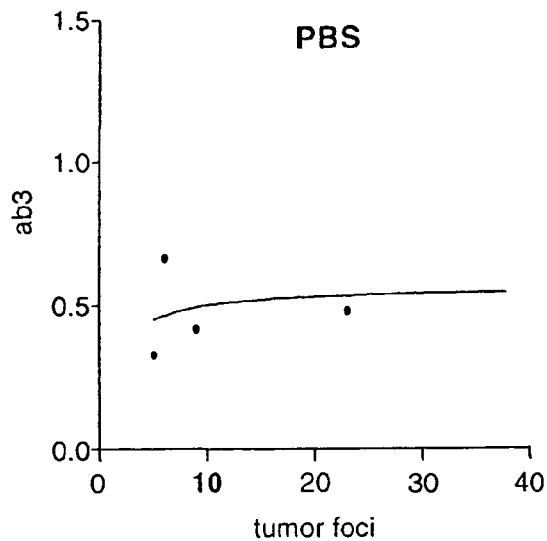
FIGS. 9A-9C show the effect of immunization with an antibody of the invention on tumor development.
Figure 9B:
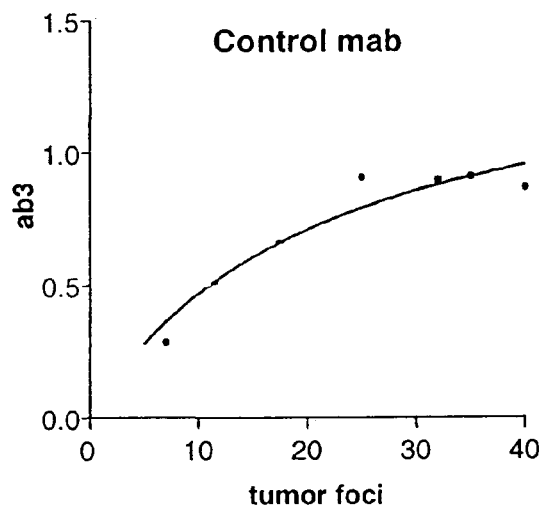
Figure 9C:
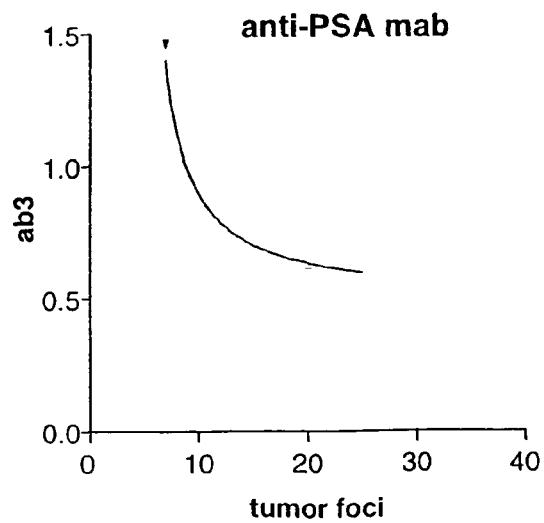

The tumor burden in the group of mice immunized with anti-PSA MAb was considerably lower compared to the group of mice immunized with control antibody. Of particular interest is the demonstration, in the group of mice immunized with anti-PSA MAb, of a negative correlation between Ab3 levels and the number of tumor foci in the lungs (FIG. 9).

Example 8

Effect of Immunization on the Induction of a Specific PSA Immunity

Figure 10A:
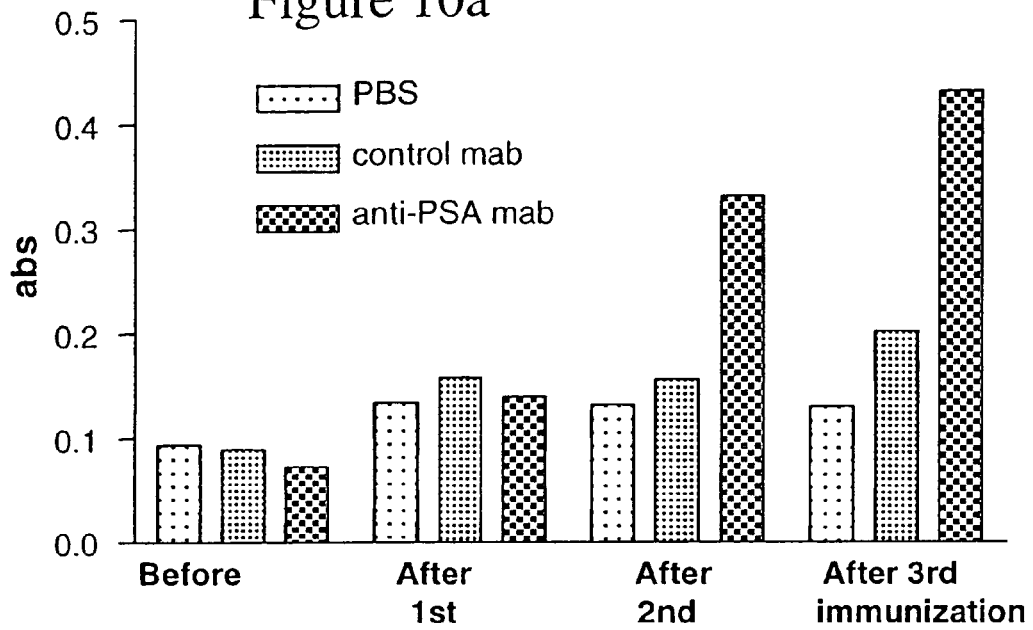
FIGS. 10A-10B show that immunizing with an antibody of the invention induces specific immunity against PSA.

We have studied in DBA mice whether the immunization with a monoclonal antibody that specifically binds to PSA (AR47.47) can result in the induction of a specific PSA immunity via the idiotypic network (i.e. induction of Ab3 antibodies). Anti-PSA antibodies (Ab3) could be detected in the serum of animals immunized with AR 47.47, a minimum of two injections of AR 47.47 was required for Ab3 production. No reactivity towards PSA was detected for the control groups (mice immunized with an isotype matched control antibody not related to PSA and mice receiving PBS injections). See FIG. 10a.

Figure 10B:
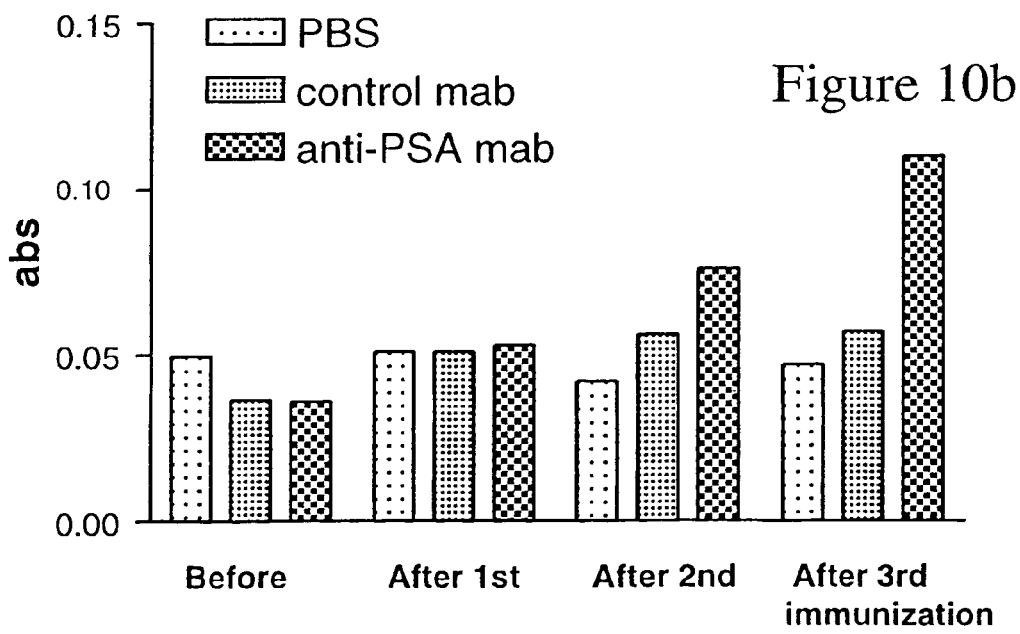

Ar 47.47 is directed toward a PSA epitope comprised between the sequence 139-163 of the PSA molecule. The anti-PSA antibodies produced by AR 47.47 immunized mice can specifically interact with the PSA peptide 139-163 (FIG. 10b). We can therefore conclude that at least part of the Ab3 produced are identical in terms of specificity to Ar 47.47. These results demonstrate that the immunization with AR 47.47 can induce a specific anti-PSA immunity in the host.

Example 9

The syngeneic tumor animals models used for these studies are:
A. Balb/cByJ mice injected intravenously with 0.1-0.04 million Line-1-PSA tumor cells. After 3-4 weeks the mice are sacrificed and the tumor burden is calculated by measuring the number of tumor foci in the lung and by measuring the weight of the lungs.
B. DBA/2 mice injected subcutaneously with 0.4 million P815-PSA cells. After 2 weeks the tumors are palpable and measured at regular intervals with a caliper. Approximately four weeks after the inoculation of the tumor cells, the mice are sacrificed, the tumors are dissected and weighed.

Therapeutic Antibodies and Control Antibodies

Therapeutic antibodies: AR47.47R6R6 a murine monoclonal antibodies of the IgG1 isotype specifically directed against PSA Control antibodies: murine monoclonal antibodies of the IgG1 isotype: CA 125 MAb directed against the tumor antigen CA125 (AltaRex Corp.) MOPC-21 a mouse myeloma immunoglobulin of unknown specificity (Sigma)

The absence of interaction between control antibodies and PSA was verified by ELISA.

The binding of the anti-PSA antibodies and control antibodies to the PSA-transfected tumor cell lines was studied by FACS analysis. None of the anti-PSA antibodies studied bound to the surface of PSA transfected tumor cells grown in vitro. The control antibodies did not bind to the surface of Line-1-PSA tumor cells. A very low binding of the two control antibodies was observed for P815-PSA cell line.

|  | AR 47.47 | | CA 125 MAb | | MOPC | |
| --- | --- | --- | --- | --- | --- | --- |
|  | negative control (mean) | AR 47.47 MAb (mean) | negative control (mean) | CA 125 MAb (mean) | negative control (mean) | MOPC MAb (mean) |
| P815-PSA | 5 | 8 | 5 | 12 | 5 | 37 |
|  | 3 | 4 | 5 | 40 | 3 | 11 |
| Line 1-PSA | 7 | 7 | 7 | 7 | 7 | 8 |
|  | 7 | 7 | 7 | 7 | 7 | 8 |
|  | 4 | 4 |  |  | 4 | 5 |

Anti-PSA antibodies and control antibodies were conjugated to KLH in order to enhance their immunogenicity in mice (glutaraldehyde conjugation, 1 mole IgG/0.2 mole KLH). The PSA binding activity of AR 47.47 after KLH-conjugation was considerably reduced by the conjugation process (90%).

|  | Experiment # | | | | |
| --- | --- | --- | --- | --- | --- |
|  | 5 | 6 | 7 | 8 | 9 |
| Mice | Balb/c | DBA | Balb/c | Balb/c | DBA |
| # mice/group | 10 | 10 | 5 | 5 | 5 |
| Therapeutic anti-PSA MAb | 47.47R6R6 | 47.47R6R6 | 47.47R6R6 | 47.47R6R6 | 47.47R6R6 |
| Control MAb | MOPC | MOPC | CA125 MAb | CA125 MAb | MOPC |
| Form of injected MAb | KLH conjugate | KLH conjugate | KLH conjugate | KLH conjugate | KLH conjugate |
| Dose of MAb per mouse/injection | 50 µg | 50 µg | 50 µg | 50 µg | 50 µg |
| Tumor cells | Line 1-PSA | P815-PSA | Line 1-PSA | Line 1-PSA | P815-PSA |
| tumor inoculation | i.v. | s.c. | i.v. | i.v. | s.c. |

|  | Experiment # | | | | |
| --- | --- | --- | --- | --- | --- |
|  | 10 | 11 | 12 | 13 | 14 |
| mice | DBA | Balb/c | DBA | Balb/c | DBA |
| # mice/group | 5 | 5 | 5 | 5 | 5 |
| Therapeutic anti-PSA MAb | 47.47R6R6 | 47.47R6R6 | 47.47R6R6 | 47.47R6R6 | 47.47R6R6 |
| Control MAb | MOPC | CA125 MAb | CA125 MAb | CA125 MAb | CA125 MAb |
| form of injected MAb | KLH conjugate | KLH conjugate | KLH conjugate | KLH conjugate | KLH conjugate |
| Dose of MAb per mouse/injection | 50 µg | 50 µg | 50 µg | 50 µg | 50 µg |
| Tumor cells | P815-PSA | Line 1-PSA | P815-PSA | Line 1-PSA | P815-PSA |
| tumor inoculation | s.c. | i.v. | s.c. | i.v. | s.c. |

Example 10

Induction of a Specific Anti-PSA Immune Response in Mice by Immunization with AR 47.47

The elicitation of a specific PSA immune response upon immunization with AR 47.47 and induction of a specific idiotypic network was studied both in Balb/c mice and DBA mice. In this set of experiments (experiments # 5, 6, 7, 9, 11, 12), the mice were first treated with either AR 47.47, control MAb or PBS, and then inoculated with PSA-transfected tumor cells. The results correspond to the measurement of the anti-idiotypic (Ab2) and anti-anti-idiotypic (Ab3) immune response against AR 47.47 before tumor inoculation.

The detection of anti-idiotypic antibodies (Ab2) was performed by ELISA using plates coated with AR 47.47 F(ab) fragments (produced by ficin digestion). The presence of Ab2 in the mouse sera of AR 47.47 immunized mice was demonstrated in experiments 7, 9, 11 and 12.

Two different ELISA assays were performed to detect the presence of Ab3. The first assay detects the binding of Ab3 on PSA coated plate. Using this assay, we have demonstrated in experiments # 5, 6 and 7 the presence of Ab3 in the sera of mice immunized with AR 47.47. The second assay employs the PSA peptide known to be recognized by AR 47.47. This assay gave positive signal for the mice immunized with AR 47.47 in experiment 7. This second assay however has not been standardized at this time and the results shown in FIG. 7 should be analyzed with caution since in many cases the positive control (performed with AR 47.47) showed negative signal. Since the PSA peptide used for this assay contains cysteine residues we believed that a cyclisation or polymerization of the peptide occurs after solubilization and/or storage of the peptide. Such effect may impairs the binding of the peptide to streptavidin coated plate or to specific antibodies (i.e. AR 47.47 or Ab3).

A competitive ELISA assay employing the PSA peptide recognized by AR 47.47 was also performed. The inhibition of the binding of PSA peptide to AR 47.47 immobilized on ELISA plate is theoretically dependent on the presence of both Ab2 and Ab3 in the mouse sera. A competitive inhibition was observed for experiments # 7, 9, 11 and 12.

These results demonstrate that an anti-idiotypic network resulting in the formation of anti-PSA antibodies by the host could be induced in mice (Balb/c and DBA) upon immunization with AR 47.47.

Example 11

Effect of AR 47.47 on Tumor Development

The ability of AR 47.47 to inhibit the development of PSA-transfected tumors was studied in both Balb/c mice (experiment # 5, 7, 11) and DBA mice (experiment 6, 9, 12). In this set of experiments the tumor inoculation occurs after treatment of the mice with either AR 47.47, control MAb or PBS. The immunization of the mice was continued after tumor inoculation.

For each experiment, the following parameters were measured: Ab2; Ab3; Ab2+Ab3; tumor burden. The results obtained for each experiment are shown in the following tables:

Effect of AR47.47-KLH Immunization on Line 1-PSA Tumor Development in Balb/c Mice

|  | # of lung tumor foci (mean ± SE) | | |
| --- | --- | --- | --- |
| experiment # | PBS | control MAb-KLH | AR47.47-KLH |
| 5 | 12.3 ± 3.2 | 8.3 ± 1.5 | 32.3 ± 2.2 |
| 7 | 26.6 ± 3.9 | 9.0 ± 1.5 | 9.6 ± 1.9 |
| 11 | 15.2 ± 1.2 | 14.8 ± 2.5 | 25.8 ± 7.5 |

| Experiment # | Ab2 Before tumor inoculation | | | Ab2 After tumor inoculation | | |
| --- | --- | --- | --- | --- | --- | --- |
|  | PBS | control MAb-KLH | AR47.47-KLH | PBS | control MAb-KLH | AR47.47-KLH |
| 5 | − | − | − | − | − | + |
| 7 | − | − | + | − | − | + |
| 11 | − | − | + | − | − | + |

| Experiment # | Ab3 Before tumor inoculation | | | Ab3 After tumor inoculation | | |
| --- | --- | --- | --- | --- | --- | --- |
|  | PBS | control MAb-KLH | AR47.47-KLH | PBS | control MAb-KLH | AR47.47-KLH |
| 5 | − | − | + | + | + | + |
| 7 | − | − | + | + | + | + |
| 11 | − | − | − | + | + | + |

| Experiment # | Ab3 peptide Before tumor inoculation | | | Ab3 peptide After tumor inoculation | | |
| --- | --- | --- | --- | --- | --- | --- |
|  | PBS | control MAb-KLH | AR47.47-KLH | PBS | control MAb-KLH | AR47.47-KLH |
| 5 | − | − | ± | + | + | + |
| 7 | − | − | + | − | − | + |
| 11 | − | − | − | − | − | − |

| Experiment # | Ab2 + Ab3 Before tumor inoculation | | | Ab2 + Ab3 After tumor inoculation | | |
| --- | --- | --- | --- | --- | --- | --- |
|  | PBS | control MAb-KLH | AR47.47-KLH | PBS | control MAb-KLH | AR47.47-KLH |
| 5 | − | − | − | − | − | + |
| 7 | − | − | + | − | − | + |
| 11 | − | − | + | − | − | + |

Effect of AR47.47-KLH Immunization on P815-PSA Tumor Development in DBA Mice

|  | % of mice without tumor | | |
| --- | --- | --- | --- |
| experiment # | PBS | control MAb-KLH | AR47.47-KLH |
| 6 | 50 | 44 | 73 |
| 9 | 60 | 60 | 100 |
| 12 | 80 | 80 | 60 |

| Experiment # | Ab2 Before tumor inoculation | | | Ab2 After tumor inoculation | | |
| --- | --- | --- | --- | --- | --- | --- |
|  | PBS | control MAb-KLH | AR47.47-KLH | PBS | control MAb-KLH | AR47.47-KLH |
| 6 | − | − | − | − | − | + |
| 9 | − | − | + | − | − | + |
| 12 | − | − | + | − | − | + |

| Experiment # | Ab3 Before tumor inoculation | | | Ab3 After tumor inoculation | | |
| --- | --- | --- | --- | --- | --- | --- |
|  | PBS | control MAb-KLH | AR47.47-KLH | PBS | control MAb-KLH | AR47.47-KLH |
| 6 | − | − | + | + | + | + |
| 9 | − | − | − | + | + | + |
| 12 | − | − | + | + | + | + |

| Ex-peri-ment # | Ab3 peptide | | | | | |
|---|---|---|---|---|---|---|
| | Before tumor inoculation | | | After tumor inoculation | | |
| | PBS | control MAb-KLH | AR47.47-KLH | PBS | control MAb-KLH | AR47.47-KLH |
| 6 | − | − | ± | + | + | + |
| 9 | − | − | − | − | ± | − |
| 12 | − | − | − | | | |

| Experi-ment # | Ab2 + Ab3 | | | | | |
|---|---|---|---|---|---|---|
| | Before tumor inoculation | | | After tumor inoculation | | |
| | PBS | control MAb-KLH | AR47.47-KLH | PBS | control MAb-KLH | AR47.47-KLH |
| 6 | − | − | − | − | − | + |
| 9 | − | − | + | − | − | + |
| 12 | − | − | + | − | − | + |

A lower tumor burden in the group of mice treated with AR 47.47 was observed in 1 experiment out of 3 for Balb/c mice tumor model and in 2 experiments out of 3 for the DBA mice tumor model. The same ELISA assays described in the previous paragraph were used to measure the humoral immune response in mice after tumor inoculation. The presence of Ab2 was detected in the groups of mice immunized with AR 47.47 in all experiments. The presence of Ab3 was detected in all groups of mice in all experiments. The positive signal obtained for Ab3 in the control groups (PBS and control mab) is not surprising since the release of human PSA by the growing tumor in vivo will induce an anti-PSA immune response.

Example 12

Effect of AR 47.47 on Tumor Progression

The ability of AR 47.47 to inhibit the progression of PSA-transfected tumors was studied in both Balb/c mice (experiment # 8, 13) and DBA mice (experiment 10, 14). In this set of experiment the tumor inoculation occurs before treatment of the mice with either AR 47.47, control MAb or PBS.

For each experiment, the following parameters were measured: Ab2; Ab3; Ab2+Ab3; and tumor burden.

The results obtained for each experiment are resumed in the following tables:

Effect of AR47.47-KLH Immunization on Line-1 PSA Tumor Progression in Balb/c Mice

| | # of lung tumor foci (mean ± SE) | | |
|---|---|---|---|
| experiment # | PBS | control MAb-KLH | AR47.47-KLH |
| 8 | 14.0 ± 4.6 | 12.8 ± 2.8 | 13.0 ± 4.7 |
| 13 | 4.2 ± 1.0 | 5.0 ± 1.1 | 7.68 ± 2.2 |

| | Ab2 | | |
|---|---|---|---|
| experiment # | PBS | control MAb-KLH | AR47.47-KLH |
| 8 | − | − | ± |
| 13 | − | − | − |

| | Ab3 | | |
|---|---|---|---|
| experiment # | PBS | control MAb-KLH | AR47.47-KLH |
| 8 | + | + | + |
| 13 | − | − | − |

| | Ab peptide | | |
|---|---|---|---|
| experiment # | PBS | control MAb-KLH | AR47.47-KLH |
| 8 | + | ± | ± |
| 13 | − | − | − |

| | Ab2 + Ab3 | | |
|---|---|---|---|
| experiment # | PBS | control MAb-KLH | AR47.47-KLH |
| 8 | − | − | + |
| 13 | − | − | − |

Effect of AR47.47-KLH Immunization on P815-PSA Tumor Progression in DBA Mice

| | % of mice without tumor | | |
|---|---|---|---|
| experiment # | PBS | control MAb-KLH | AR47.47-KLH |
| 10 | 100 | 100 | 100 |
| 14 | 100 | 100 | 80 |

| | Ab2 | | |
|---|---|---|---|
| experiment # | PBS | control MAb-KLH | AR47.47-KLH |
| 10 | − | − | + |
| 14 | − | − | + |

| | Ab3 | | |
|---|---|---|---|
| experiment # | PBS | control MAb-KLH | AR47.47-KLH |
| 10 | + | + | + |
| 14 | − | + | + |

|  | Ab peptide | | |
| --- | --- | --- | --- |
| experiment # | PBS | control MAb-KLH | AR47.47-KLH |
| 10 | − | − | − |
| 14 | − | − | − |

|  | Ab2 + Ab3 | | |
| --- | --- | --- | --- |
| experiment # | PBS | control MAb-KLH | AR47.47-KLH |
| 10 | − | − | + |
| 14 | − | − | − |

No therapeutic effect on tumor progression was observed for AR47.47. However it should be taken into consideration that the growth rate of tumors in mice far exceed the time required for the development of an appropriate therapeutic immune response capable to eradicate or slow tumor progression. Also the growth rate of tumor in mice do not reflect what is happening in humans since prostate cancer is considered to be a slow progressing disease.

Example 13

Possible Mechanism of Action

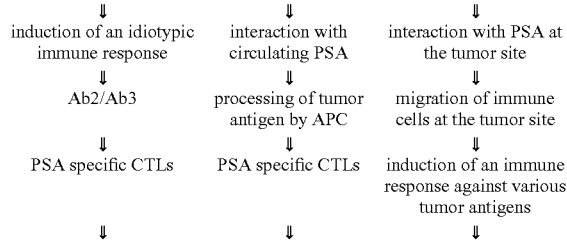

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings.

We claim:

1. A composition for the treatment of prostate cancer, comprising a composition comprising an isolated antibody or antigen-binding fragment thereof produced by a hybridoma having ATCC Accession No. 12526 that specifically binds to circulating PSA (Prostate Specific Antigen) and induces a therapeutic immune response, and wherein the binding of the antibody or antigen-binding fragment thereof to PSA is not inhibited by the polypeptide of SEQ ID NO: 2, 3 or 4.

2. The composition of claim 1, wherein the antibody or antigen binding fragment thereof binds to an epitope of amino acid residues 139 to 163 of PSA (SEQ ID NO: 1).

3. The composition of claim 1, wherein the therapeutic immune response comprises a humoral and cellular immune response.

4. A composition for treating prostate cancer, comprising an isolated antibody or antigen-binding fragment thereof produced by a hybridoma having ATCC Accession No. 12526 that specifically binds to an epitope of circulating PSA, the antibody or antigen binding fragment thereof being capable of binding to the antigen to form an immunogenic antibody or antigen binding fragment thereof antigen complex, and wherein the binding of the antibody or antigen-binding fragment thereof to PSA is not inhibited by the polypeptide of SEQ ID NO: 2, 3, or 4.

5. A composition for inducing an immune response, comprising an isolated antibody or antigen-binding fragment thereof produced by a hybridoma having ATCC Accession No. 12526 that specifically binds to an epitope of circulating PSA, the antibody or antigen binding fragment thereof being capable of binding to the antigen to form an immunogenic antibody or antigen binding fragment thereof antigen complex, and wherein the binding of the antibody or antigen-binding fragment thereof to PSA is not inhibited by the polypeptide of SEQ ID NO: 2, 3, or 4.

6. A composition for increasing the immunogenicity of PSA, comprising an isolated antibody or antigen-binding fragment thereof produced by a hybridoma having ATCC Accession No. 12526 that specifically binds to an epitope of circulating PSA, the antibody or antigen binding fragment thereof being capable of binding to the antigen to form an immunogenic antibody or antigen binding fragment thereof antigen complex, and wherein the binding of the antibody or antigen-binding fragment thereof to PSA is not inhibited by the polypeptide of SEQ ID NO: 2, 3, or 4.

7. The composition of claim 1, wherein the antibody or antigen-binding fragment thereof is conjugated to an immunogenic carrier.

8. The composition of claim 7, wherein the immunogenic carrier is keyhole limpet hemocyanin.

9. The composition of claim 2, wherein the binding agent is conjugated to an immunogenic carrier.

* * * * *